(12) United States Patent
Bateman et al.

(10) Patent No.: US 9,302,889 B2
(45) Date of Patent: *Apr. 5, 2016

(54) HOISTING DEVICE AND SYSTEM AND METHOD FOR USING THE SAME

(71) Applicant: JERGENS, INC., Cleveland, OH (US)

(72) Inventors: Jason Bateman, Mentor, OH (US); Bob Kucinic, Solon, OH (US)

(73) Assignee: Jergens, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/710,806

(22) Filed: May 13, 2015

(65) Prior Publication Data

US 2015/0246793 A1    Sep. 3, 2015

Related U.S. Application Data

(63) Continuation of application No. 14/486,790, filed on Sep. 15, 2014, now Pat. No. 9,067,766.

(60) Provisional application No. 61/878,075, filed on Sep. 16, 2013, provisional application No. 62/025,377, filed on Jul. 16, 2014.

(51) Int. Cl.
| | |
|---|---|
| *B66F 19/00* | (2006.01) |
| *B66C 13/16* | (2006.01) |
| *B66C 1/66* | (2006.01) |
| *G01N 3/08* | (2006.01) |
| *G01L 1/22* | (2006.01) |
| *B66C 15/06* | (2006.01) |

(52) U.S. Cl.
CPC . *B66C 13/16* (2013.01); *B66C 1/66* (2013.01); *B66C 15/065* (2013.01); *G01L 1/22* (2013.01); *G01N 3/08* (2013.01)

(58) Field of Classification Search
CPC ............ B66C 1/66; B66C 13/16; G01L 1/22; G01N 3/08
USPC ..................... 294/215, 82.1; 403/78, 79, 164; 410/101–116
See application file for complete search history.

(56) References Cited

U.S. PATENT DOCUMENTS

| | | |
|---|---|---|
| 3,492,033 A | 1/1970 | Mueller |
| 3,827,514 A | 8/1974 | Bradley |

(Continued)

FOREIGN PATENT DOCUMENTS

WO    2008/007961 A3    1/2008

OTHER PUBLICATIONS

"Strain gauge", Wikipedia; http://en.wikipedia.org/wiki/Strain_gauge; Published Apr. 12, 2014; Retrieved from Internet Apr. 21, 2014.

(Continued)

*Primary Examiner* — Gabriela Puig
(74) *Attorney, Agent, or Firm* — Rankin, Hill & Clark LLP

(57) ABSTRACT

A hoisting device and, more particularly, an intelligent hoist ring that is capable of monitoring, recording and/or communicating the use of the hoist ring including monitoring, recording and/or communicating the loads on the hoist ring that can be used, inter alia, to determine condition of the hoist ring and whether it can remain in active service and monitoring tightening loads independently of applied loads.

14 Claims, 21 Drawing Sheets

(56) References Cited

U.S. PATENT DOCUMENTS

| | | | |
|---|---|---|---|
| 3,918,301 A | 11/1975 | Baer | |
| 4,153,123 A | 5/1979 | Bereyziat | |
| RE30,183 E | 1/1980 | Popenoe | |
| 4,294,122 A | 10/1981 | Couchman | |
| 4,428,240 A | 1/1984 | Schoeps | |
| 4,641,986 A * | 2/1987 | Tsui et al. | 403/164 |
| 4,705,422 A * | 11/1987 | Tsui et al. | 403/60 |
| 4,899,591 A | 2/1990 | Kibblewhite | |
| 5,222,849 A | 6/1993 | Walton | |
| 5,226,765 A | 7/1993 | Walton | |
| 5,286,130 A | 2/1994 | Mueller | |
| 5,291,789 A | 3/1994 | Walton | |
| 5,352,056 A | 10/1994 | Chandler | |
| 5,388,463 A | 2/1995 | Scott | |
| 5,405,210 A | 4/1995 | Tsui | |
| 5,584,627 A | 12/1996 | Ceney et al. | |
| 5,586,801 A | 12/1996 | Sawyer et al. | |
| 5,634,734 A | 6/1997 | Schron, Jr. et al. | |
| 5,745,042 A | 4/1998 | Pratt | |
| 5,848,815 A | 12/1998 | Tsui et al. | |
| 6,009,759 A | 1/2000 | Kibblewhite et al. | |
| 6,068,310 A | 5/2000 | Fuller et al. | |
| 6,267,422 B1 * | 7/2001 | Alba | 294/215 |
| 6,443,514 B1 | 9/2002 | Fuller et al. | |
| 6,501,211 B1 | 12/2002 | Nasrollahzadeh | |
| 6,652,012 B1 | 11/2003 | Fuller et al. | |
| 6,749,237 B1 | 6/2004 | Ma | |
| 6,764,259 B1 | 7/2004 | Preta | |
| 6,953,212 B2 * | 10/2005 | Alba | 294/217 |
| 7,114,872 B2 * | 10/2006 | Alba | 403/78 |
| 7,246,980 B2 | 7/2007 | Azzalin et al. | |
| 7,412,898 B1 | 8/2008 | Smith et al. | |
| 8,024,980 B2 | 9/2011 | Arms et al. | |
| 8,201,867 B2 * | 6/2012 | Thomeczek | 294/215 |
| 8,562,053 B2 * | 10/2013 | Davidson et al. | 294/215 |
| 2002/0149216 A1 | 10/2002 | Teixeira | |
| 2003/0000314 A1 | 1/2003 | Smith et al. | |
| 2004/0190591 A1 | 9/2004 | Zhang | |
| 2006/0022056 A1 | 2/2006 | Sakama et al. | |
| 2013/0064622 A1 | 3/2013 | Mekid et al. | |

OTHER PUBLICATIONS

"Measuring Strain with Strain Gages"; National Instruments; http://www.ni.com/white-paper/3642/en/; Published Apr. 9, 2014; Retrieved from Internet Apr. 21, 2014.

"Strain gauges"; Lessons in Electric Circuits, vol. 1-DC, Chapter 9.7 Electrical Instrumentation Signals, All About Circuits; http://www.allaboutcircuits.com/vol_1/chpt_9/7.html; Retrieved from Internet Apr. 21, 2014.

* cited by examiner

HOISTING DEVICE AND SYSTEM AND METHOD FOR USING THE SAME

This application is a continuation of pending U.S. patent application Ser. No. 14/486,790 filed on Sep. 15, 2014 (Our Ref. JER-37120.02), which claims priority in provisional patent application Ser. No. 61/878,075 that was filed on Sep. 16, 2013 and provisional patent application Ser. No. 62/025,377 that was filed on Jul. 16, 2014, which are both incorporated by reference herein.

The invention of this application relates to hoisting device and, more particularly, to an intelligent hoist ring that is capable of monitoring, recording and/or communicating the use of the hoist ring. Yet more particularly, to monitoring, recording and/or communicating the loads applied to the hoist ring that can be used, inter alia, to determine condition of the hoist ring and whether it can remain in active service.

BACKGROUND OF THE INVENTION

There are a wide range of lifting and/or hoisting devices used in the industry which include, but are not limited, to center-pull style hoist rings. These devices are used to lift a variety of heavy loads or objects, such as die sets and molds. However, while the invention has been found to work particularly well with these center-pull hoist rings wherein it is being described below in connection with center-pull hoist rings, the invention has broader applications and may be used for a variety of applications where it is necessary to monitor, record and communicate applied loads over the service life of the device. These applications can include the use of a hoist ring used to lift structures such as containers, aircrafts, vehicles, boats, equipment, dies, tooling, molds, rigging, windmills, etc.

Through the years, a large number of hoisting devices have been developed which allow for a ring to be connected to the hook of a hoist wherein the ring pivots and/or swivels for the purpose of automatically adjusting the disposition of the ring with respect to the force being applied to the hoist during the lifting procedure. Such devices are found in patents incorporated by reference herein which will be discussed more below.

The center-pull hoist devices have a post assembly that allows 360-degree rotation of a support or body member. The rotating support member carries the load lifting ring, which can be in many forms include the form of a U-shaped clevis or bail. The clevis can pivot about a center clevis axis of the rotating support member and has a pivot arc of about 180 degree (bail angle).

Like the center-pull style, the side-pull hoist ring includes a rotating support member mounted onto the load by a post assembly. In a side-pull hoist ring, the support member can be generally U-shaped to define an outer bite portion in which a circular load ring is pivotally mounted. The circular load ring is offset from the axis of the center post assembly.

These prior patents include the device shown in Schron Jr. et al U.S. Pat. No. 5,634,734 that discloses a center-pull style hoist device and is incorporated by reference for showing the same. Also incorporated by reference are the Ma U.S. Pat. No. 6,749,237, the Tsui U.S. Pat. Nos. 5,405,210 and 5,848,815, the Sawyer et al U.S. Pat. No. 5,586,801, and the Chandler U.S. Pat. No. 5,352,056 that all show different styles of center-pull hoist ring.

Fuller et al U.S. Pat. No. 6,652,012; Fuller et al U.S. Pat. No. 6,443,514; and Fuller et al U.S. Pat. No. 6,068,310 all disclose side-pull hoisting devices and are incorporated by reference for showing the same.

All of these device disclose effective hoisting devices that have been used effectively in the industry for many years and which are provided as background for the invention of this application.

In addition to the above-described hoisting devices, also known in the patent art is a patent to Mueller U.S. Pat. Nos. 5,286,130, and 3,492,033 which disclose a clevis hoist ring assembly. The Mueller patents are incorporated by reference for showing yet another style of hoist ring that could utilize with the invention of this application However, while hoist rings are designed to be very robust, every hoist ring has a predetermined load limit based on the size and design of the ring. And, if a predetermined load limit is exceeded, the ring can be damaged. Thus, when a hoist ring is utilized to lift or support a critical load, it is important to know whether the ring has been damaged by its use on prior loads. Therefore, when dealing with critical loads, hoist rings are often pulled out of service to test the rings to ensure that there has been no damage to the ring during prior use. As can be appreciated, this can be costly and can remove the ring from service for an extended amount of time over its service life. This is especially true if there is no data on the prior use. Therefore, the service intervals of existing hoist rings must be set based on the worst case scenarios instead of the actual use of the ring. However, if the service life of the ring could be monitored, both the service life of the ring could be extended and the service intervals could be determined based on the actual use of each ring individually thereby minimizing the amount of time the ring is out of service throughout its service life. Therefore, there is a need for a hoist ring that can monitor its own use and store data associated with this use such that service intervals can be based on actual use of each hoist ring.

SUMMARY OF INVENTION

The invention of this application relates to a hoist ring and, more particularly, an intelligent hoist ring that can measure, record and/or communicate the use of the hoist ring to condition of the ring that can be used to help determine the optimal service intervals and/or life for the ring. More particularly, the invention of this application relates to a system of comprehensive hoist ring hardware, software and/or external devices for purposes of reading forces applied to the ring, recording these applied forces, calculating the effect of the applied forces on the structures of the ring and/or communicating these forces and/or data wherein informed decision can be made concerning service intervals, service life, design improvements, hoist ring selection based on the reported force for the hoist ring to meet mechanical design and functional requirements.

More particularly, in accordance with certain aspect of the present invention provided is a hoisting device that includes a hoist body that is selectively attachable to an object to be lifted and/or secured and a hoist ring attached to the body. The hoisting device further includes one or more sensors to measure the loads that are applied to the hoist ring.

According to other aspects of the present invention, the hoisting device can further include a data storage device to record data on the applied loads. This can include the measuring and recording of any data that is deemed to be important to the service life of the device and/or the use of the device. This can include, but is not limited to, the loads applied to the ring, the duration of the load, the nature of the load, the direction of the load, and/or any impact loads.

According to yet further aspects of the present invention, the hoisting device can further include an angle measurement feature that can monitor and record the load angle of the applied load and/or bail angle of the ring when the load is applied. The greater the load angle and/or bail angle, the greater the overall applied load. As is known in this field, the load applied to the ring produces stresses in the ring and these stresses can change based on load angle. Typically, the stresses in the ring increase as the bail angle of the applied load increases. Yet further, there are limits on the bail angle that are to be applied to the hoist ring. Therefore, the intelligent ring of this application can be configured to measure the bail angle of the load in combination with the amount of load, record this data and even communicate this data. If a load is applied that is outside the limits of the load and/or bail angle, this can be recorded. This can include, but is not limited to multiple sensors positioned circumferentially around the hoist ring bolt and/or sensors to determine the bail angle of the ring of the hoist ring.

According to even yet further aspects of the present invention, the hoisting device can further include external notification features. This can include, but is not limited to, an alert feature that the hoist ring bolt is properly tightened to the load with a desired bolt holding force or load, a warning feature that the applied load is too great, a warning feature that a shock load has been encountered, a warning feature that the bail or load angle is outside a predetermined range, a warning feature that a service interval has been reached, a warning feature that any predetermined load limits have been surpassed and/or a warning feature that any noteworthy event has occurred.

According to other aspects of the present invention, the hoisting device can further include software to analyze the data from the sensors and/or to help determine if a predetermined limit has been surpassed and/or an event has occurred.

Yet further aspects of the invention include systems to measure, store and communicate resultant data within the hoist ring itself and/or to ancillary software packages and hardware devices.

Yet even further, it is an object of the invention to achieve the intelligent hoist ring design without significant changes to the mechanical structure of existing hoist ring designs. This can include a sensor device that can replace the existing washer in an existing hoist ring.

According to further aspects and objects of the invention, the bolt holding load and the lifting loads can be calculated based on actual load readings and not based on calculations from material deflection and/or elongation.

According to yet further aspects and objects of the invention, the holding loads and the lifting loads are calculated based on one or more compression sensors.

According to another set of aspects and objects of the invention, two sets of compression sensors are provided such that the lifting force or load can be read, recorded and communicated separately from the holding force or load of the main bolt.

According to a further set of aspects and objects of the invention, provided is an internal power source to power the internal electronics including the compression sensor(s) and/or strain gauges as needed and/or to provide a power supply that meets mechanical design requirements and, in certain embodiments, a power source that can be replenished.

According to another set of embodiments, the system can communicate readings from gage(s) and/or sensors to a decision making device.

According to even yet other sets of embodiments, the hoist ring device can include a system to measure and record load readings (audit trail); a system measure and record a shock readings (sharp momentary load); a system measure and record torque on the bolt; a system measure and record lift rand; a system measure and record equality of the load; a system measure and record bail angle (applied load effect); evaluate a load readings; interpret reading to illuminate an appropriate status light (such as a micro sized light source (red light—alert; green light—normal operation; yellow light—caution and/or maintenance needed); communicate with a calibration station and/or hand-held device; provide traceable location/identification signatures (such as a hard wired cable, RFID, GPS information, WI-FI and ZiGbee); provide a hoist ring design and system design that allows for field retro-fit to existing end-users hardware; provide a system that is scalable to allow for the incorporation of additional sensory hardware and/or software; provide a system that can interface and/or establish communications to and from a mobile and fixed electronic units, provide a system that includes an interface for reading audit trail and provides for output reporting; provide a system that includes an interface for calibration of bolt for Proof Test Process; provide a system that includes an interface for the ID/Locating requirements; provide a system that includes an interface to reset of fault and/or warning light; provide a system that includes an interface for evaluating the cycles of the hoisting device (such as how many lifts the device has been used on); provide a system that includes a database structure with appropriate query capability for designated end users to monitor the construction, re-certification, and/or disposition of damaged unit; provide a system that allows for the creation of customized reports; and/or provide a system that includes internal and/or secondary software and systems that can be used by authorized service personnel and/or the end users, and/or in house safety coordinator to monitor the usage and function of the hoist ring.

According to yet further aspect of the invention of this application, the hoisting device is a Center-Pull hoist ring of varying sizes. In particular, the hoist ring and corresponding sensing devices can be configured to work with any bolt size including, but not limited to, any English or Metric sized bolt; any pitch, diameter, thread size and/or style bolt. Yet even further, it is contemplated that the invention of this application can work with hoist rings that use fasteners other than threaded bolt fasteners. Yet even further, the disk that is utilized to obtain, manage, record and/or analyze the data can be configured to work with more than one size, style and/or configuration of hoist ring.

According to even yet further aspects of the invention, provided is a hoist ring that is a self contained electro-mechanical hoist ring device that can dynamically, in real-time, provide a visual queue to a end-user that a lift is within proof tested limits. In this respect, the device of this application can include a real time warning light that can be used as a visual indicator to stop or to use a warning sound and/or communicated warning to an external device or system. The system can be configured to allow the warning light (or system) to signal when a lift has exceeded the proof limit through continuous lift and/or shock. Thus, the warning light (or system) can be used to warn the end-user and indicate that the lifting device is to be serviced/evaluated. During servicing/evaluation, if it is determined that the hoist device is within design parameters, then the warning light(s) can be reset, and the device returned to service.

According to another set of aspects of the invention, provided is a hoist ring that is a self contained electro-mechanical hoist ring device that can dynamically, in real-time, provide a visual queue to a end-user that a lift is within proof tested limits. In this respect, the device of this application also can include one or more strain gauges that can be configured to detect and/or determine tightening loads to ensure that the hoist ring bolt is properly tightened to the load with a desired bolt holding force or load, applied loads to warn if the applied load is too great, shock loads to warn if the ring has been subjected to a large shock load, bail angle or load angle to make sure it is not outside a predetermined range, and/or other loads.

Also incorporated by reference herein are a Wikipedia article on Strain Gauges dated Apr. 21, 2014 that discloses background information on these types gauges, a document titled MEASURING STRAIN WITH STRAIN GAUGES from National Instruments dated Apr. 9, 2014 and a document titled STRAIN GAUGES from allaboutcircuits.com dated Apr. 21, 2014. All of these documents provide background information on strain gauges and these documents are incorporated by reference into this application for showing the same.

These and other objects, aspects, features, developments and advantages of the invention of this application will become apparent to those skilled in the art upon a reading of the Detailed Description of Embodiments set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which form a part hereof and wherein.

DETAILED DESCRIPTION OF EMBODIMENTS

Figure 1:
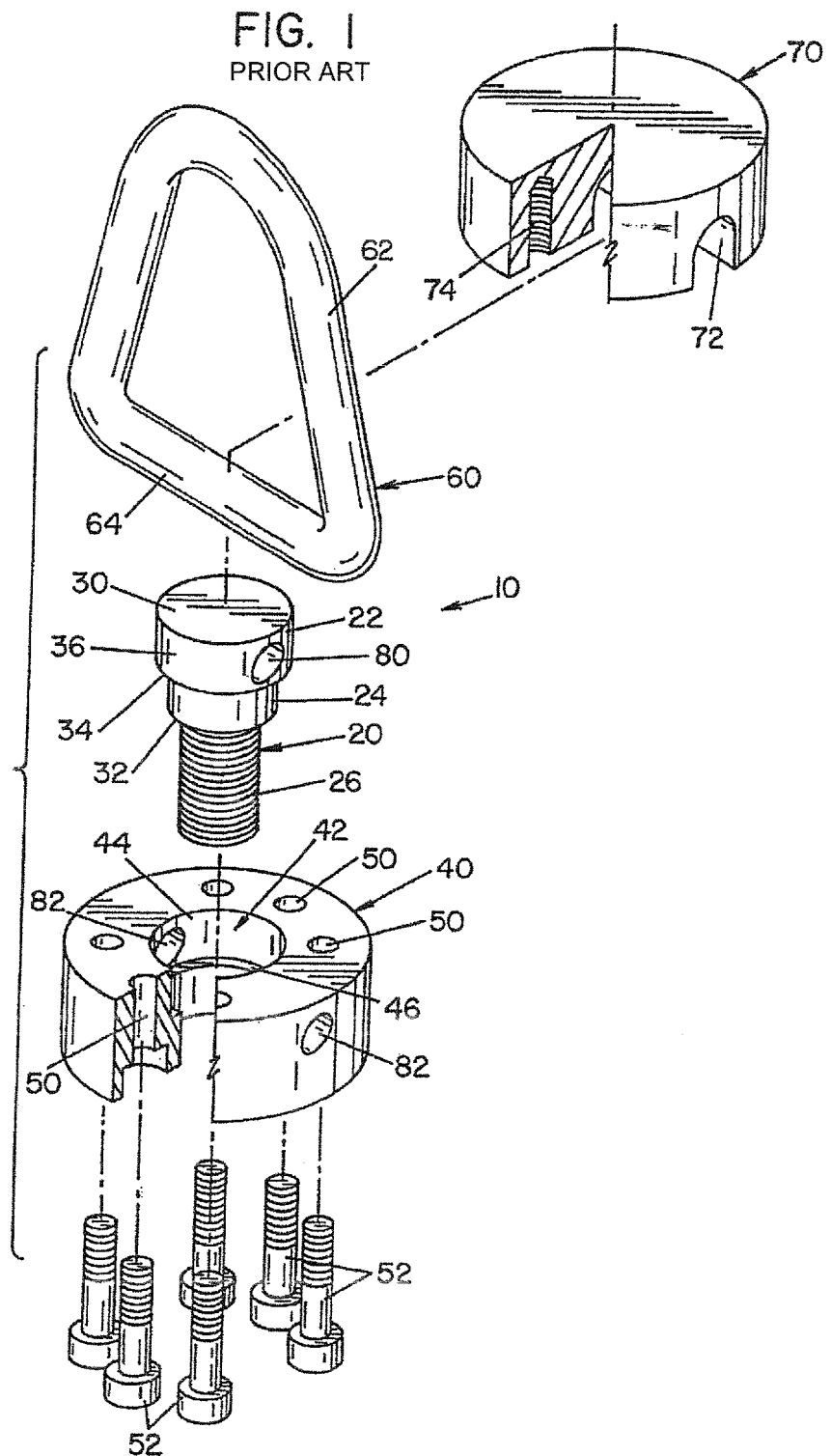
FIG. 1 is an exploded view of a prior art center-pull hoist ring showing certain aspects of a center-pull hoist ring for practicing the present invention.
Figure 3:
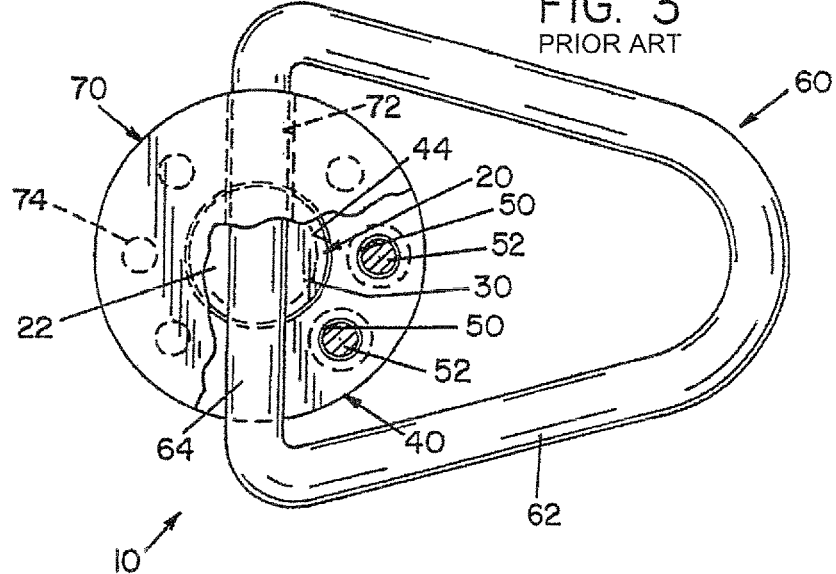
FIG. 3 is a top view somewhat cut away of the example prior art center-pull hoist ring shown in FIG. 1.
Figure 2:
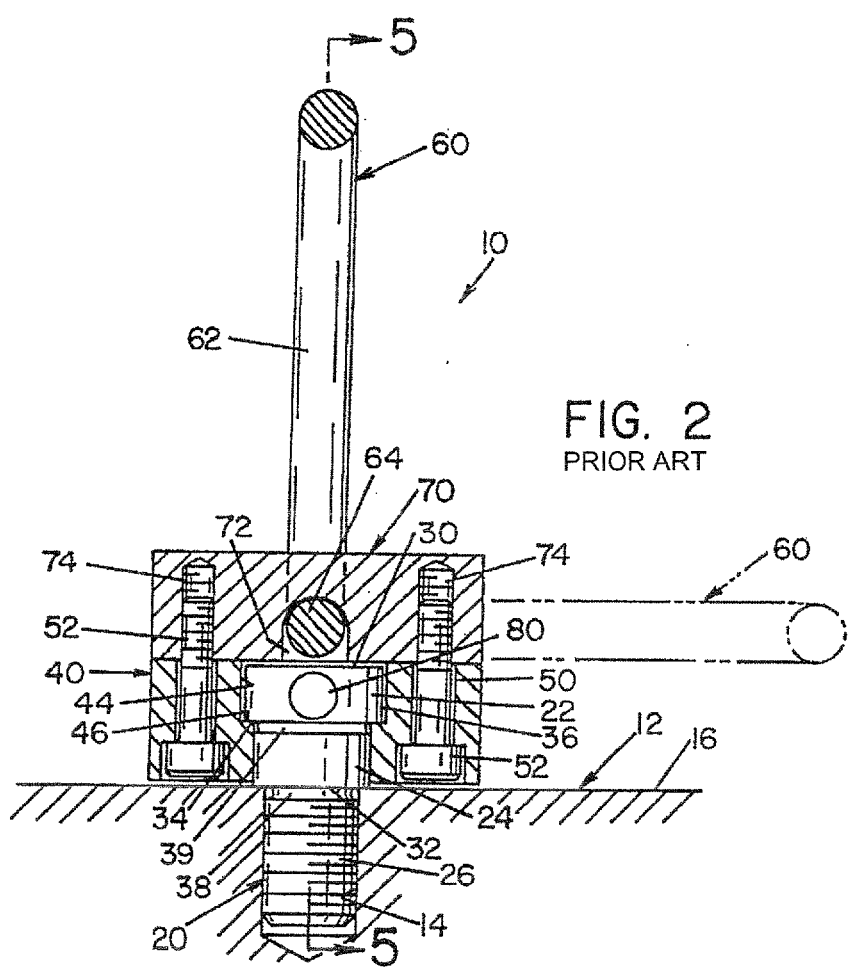
FIG. 2 is a side, partially cross-section view of the example prior art center-pull hoist ring shown in FIG. 1.
Figure 4:
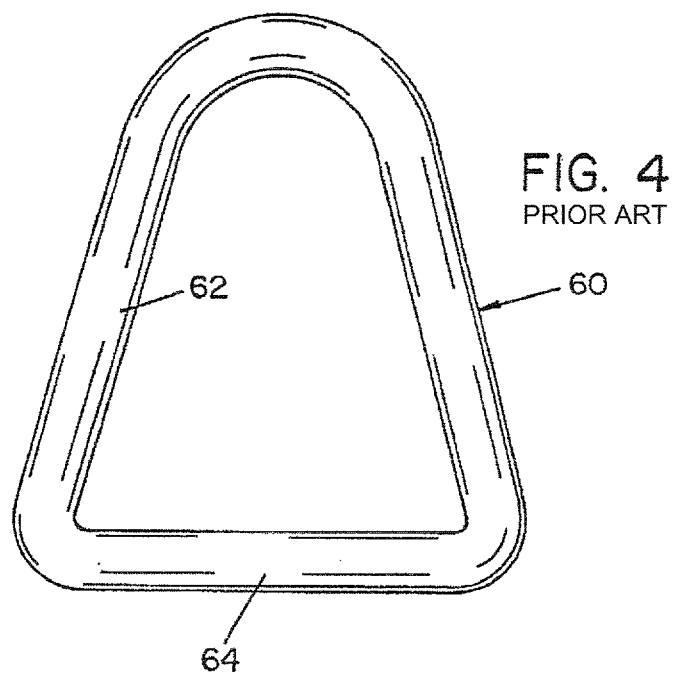
FIG. 4 is a side view of a ring portion for the example prior art center-pull hoist ring shown in FIG. 1.
Figure 5:
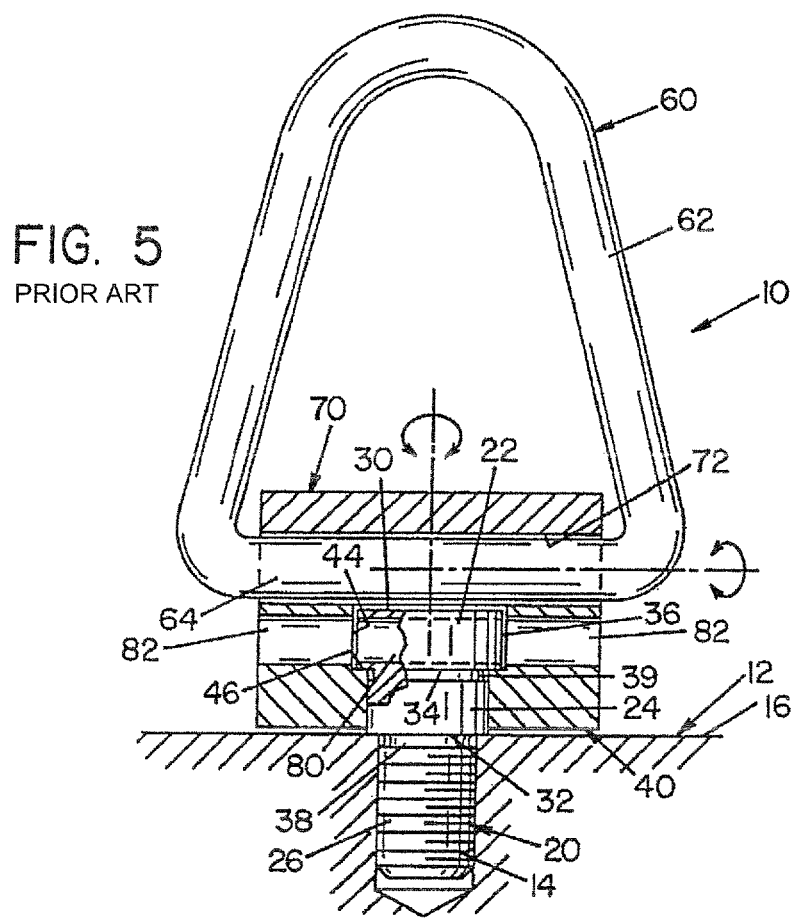
FIG. 5 is a cross-sectional view take on lines 5-5 of FIG. 2, showing certain operating characteristics of the example prior art center-pull hoist ring shown in FIG. 1.
Figure 6:
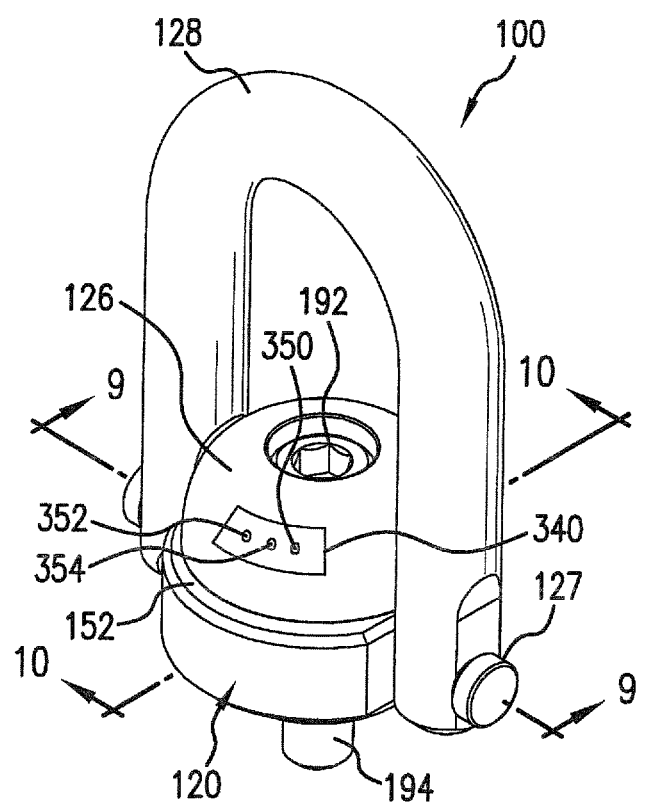
FIG. 6 is a rear perspective view of a set of embodiments of an intelligent center-pull hoist ring showing certain aspects of the present invention of this application.
Figure 7:
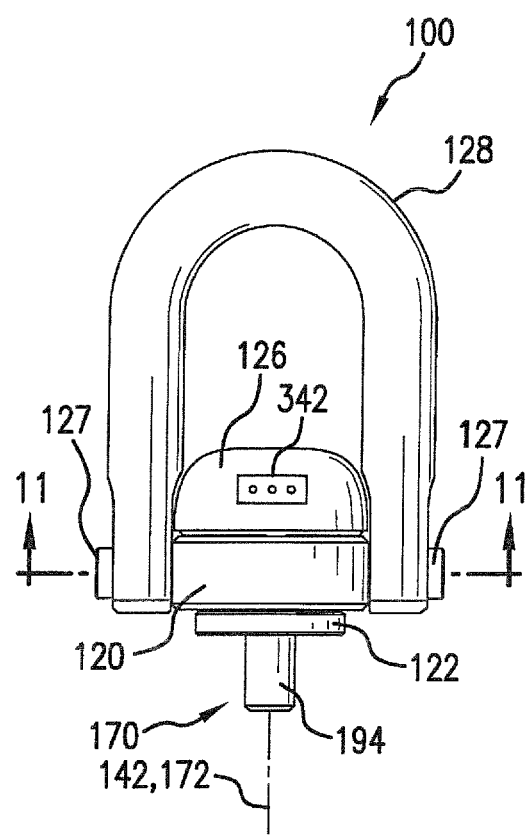
FIG. 7 is a front side view of the center-pull hoist ring shown in FIG. 6.
Figure 8:
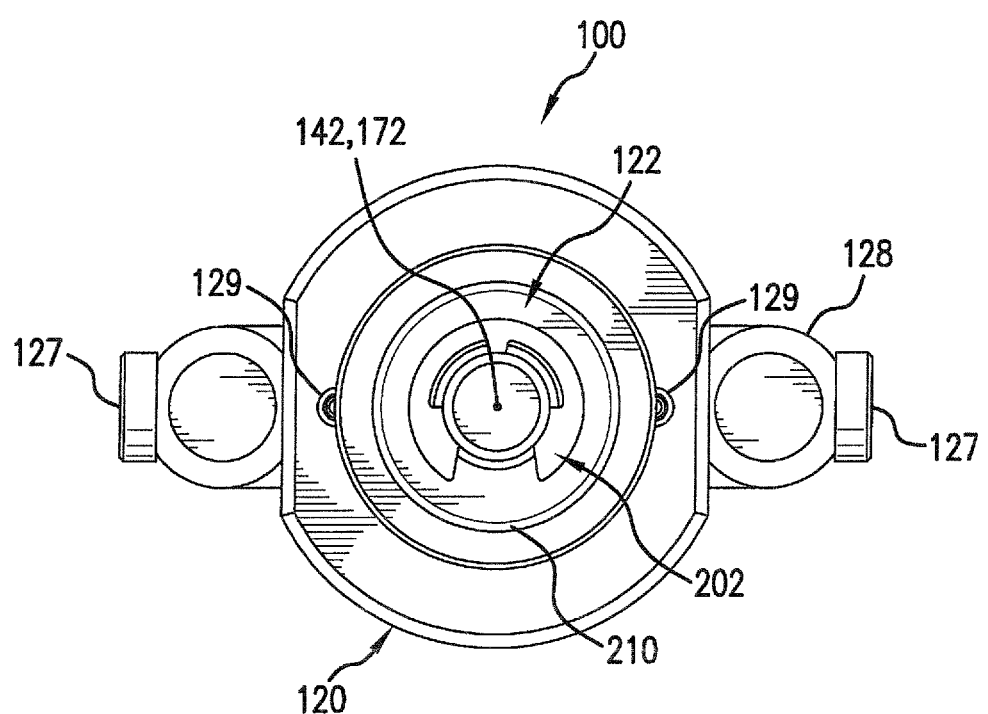
FIG. 8 is a bottom view of the center-pull hoist ring shown in FIG. 6.
Figure 9:
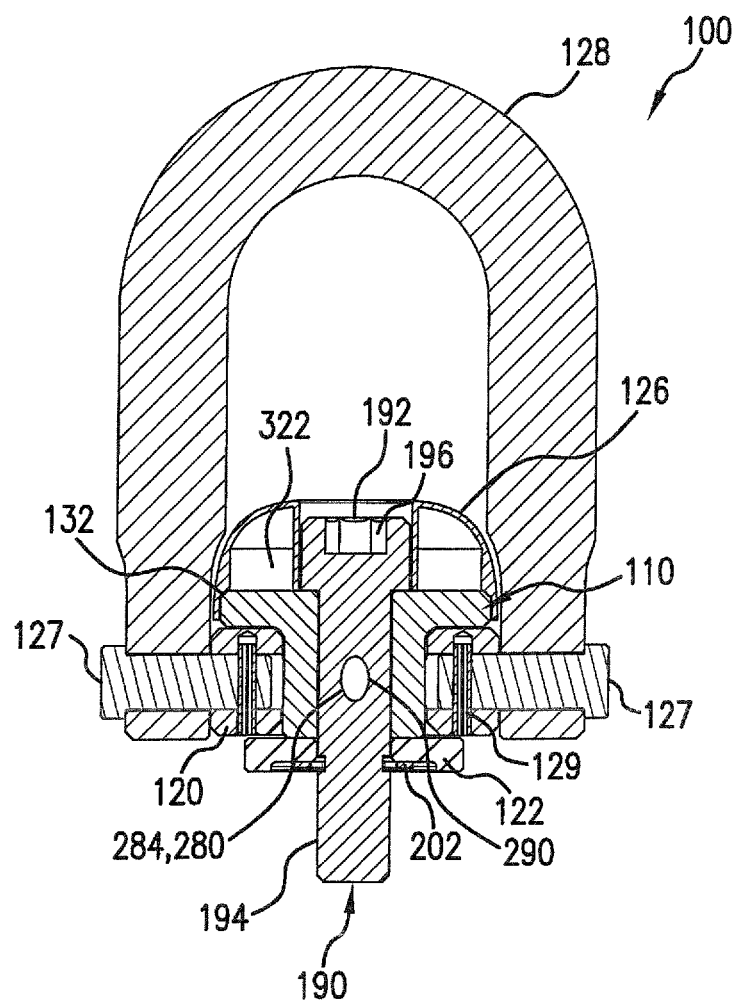
FIG. 9 is a sectional view taken along line 9-9 in FIG. 6.
Figure 10:
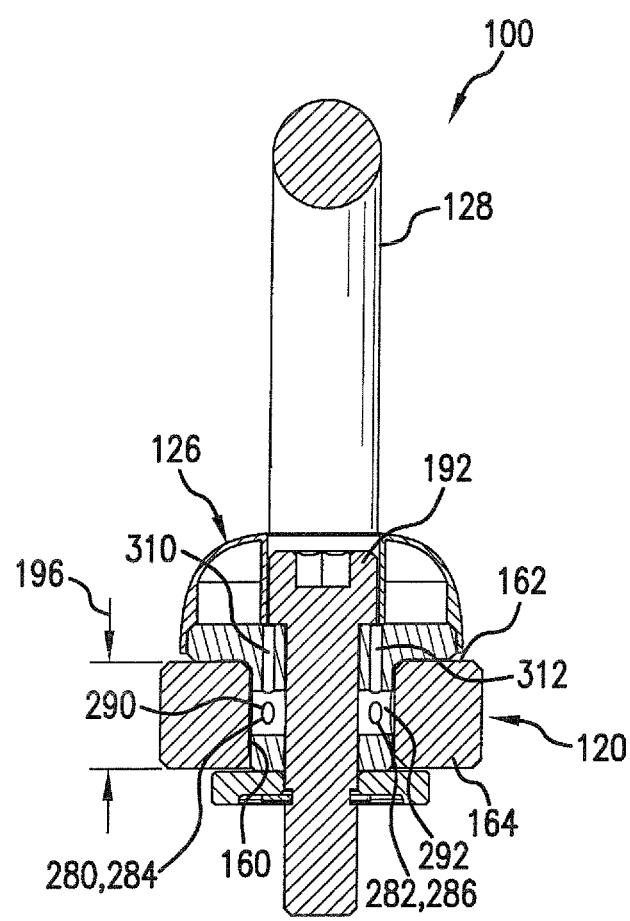
FIG. 10 is a sectional view taken along line 10-10 in FIG. 6.
Figure 11:
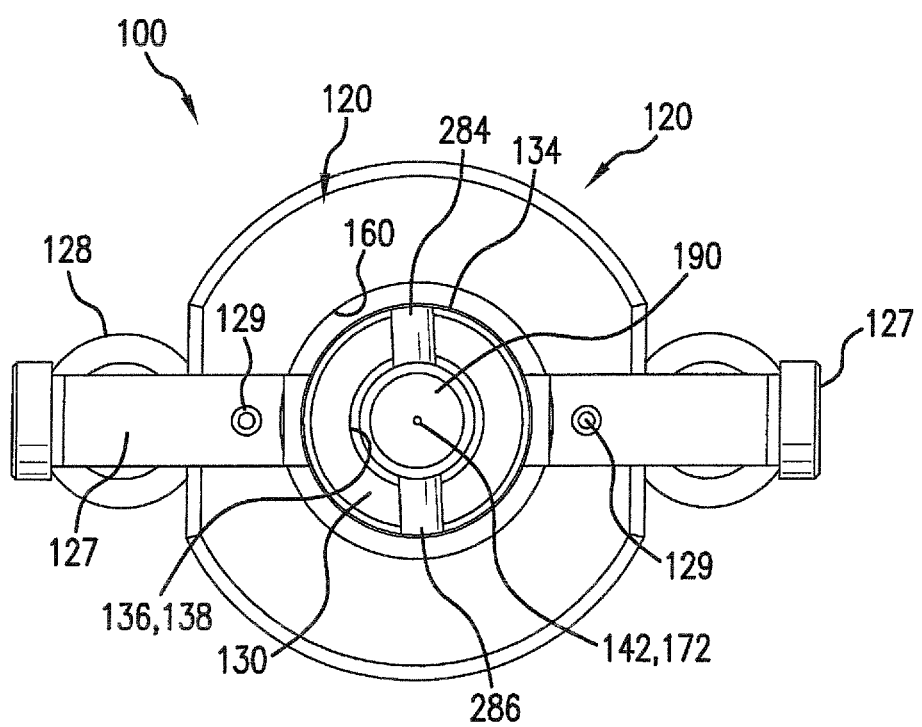
FIG. 11 is a sectional view taken along line 11-11 in FIG. 6.
Figure 12:
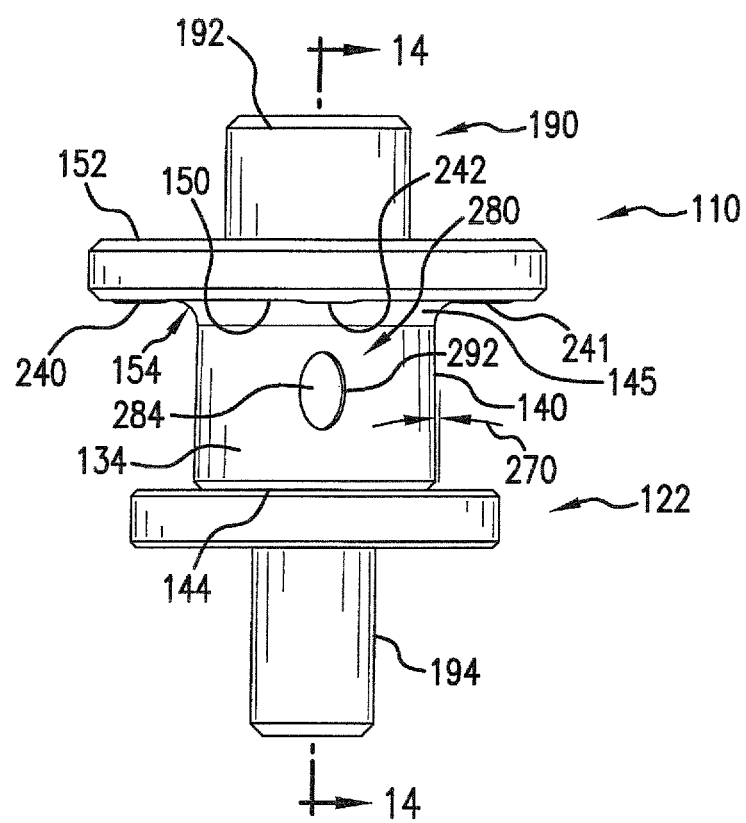
FIG. 12 is a side view of the certain components of the center-pull hoist ring shown in FIG. 6.
Figure 13:
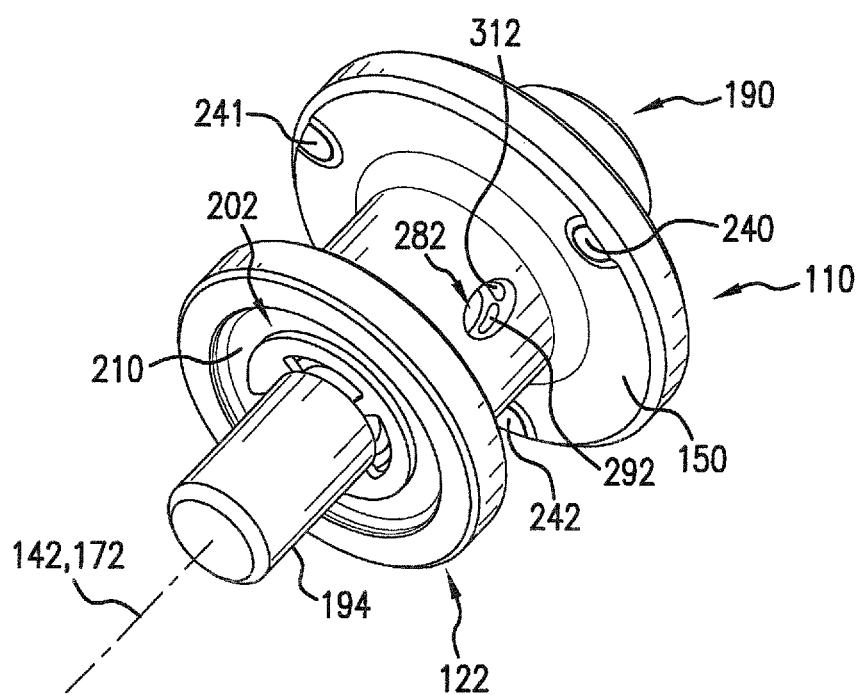
FIG. 13 is a bottom perspective view of the components shown in FIG. 12.
Figure 14:
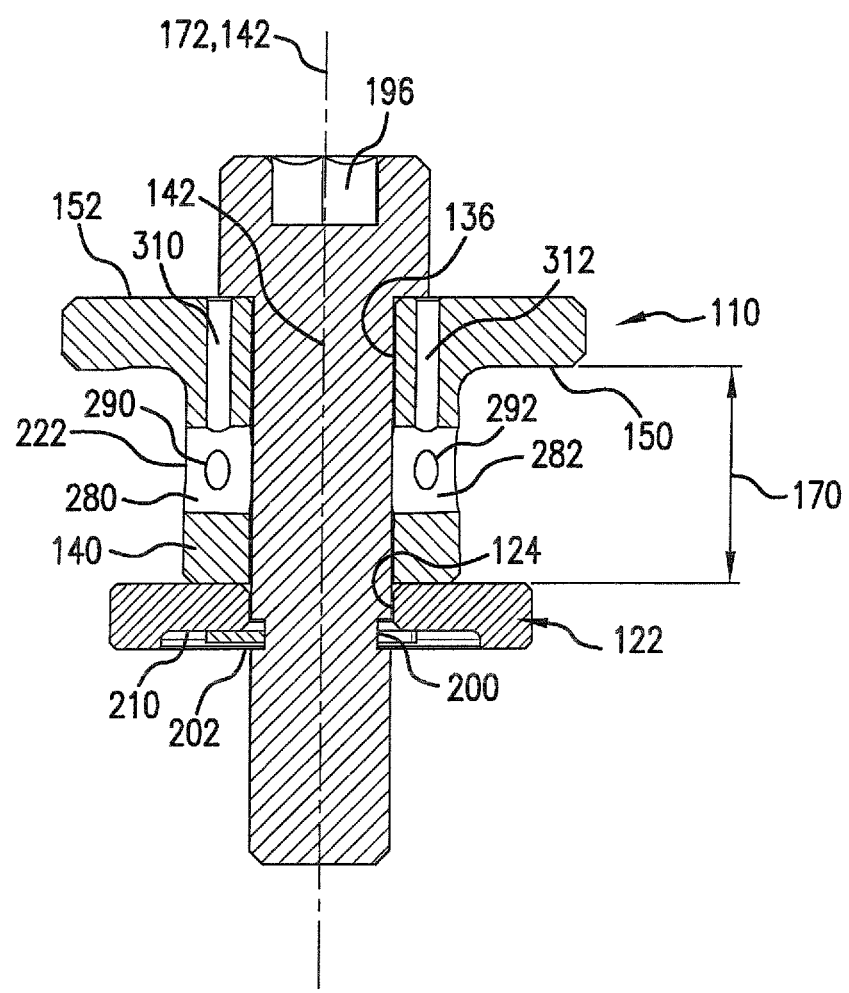
FIG. 14 is a sectional view taken along line 14-14 in FIG. 12.
Figure 15:
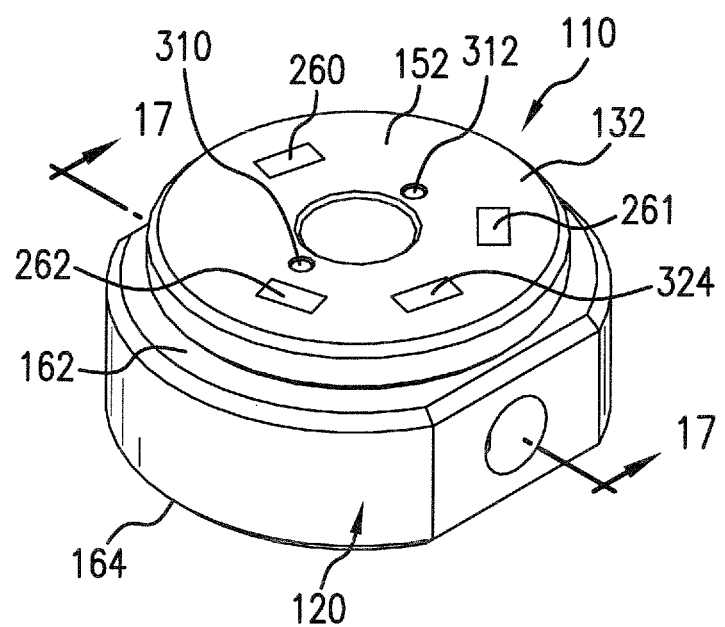
FIG. 15 is a perspective view of the another set of components of the center-pull hoist ring shown in FIG. 6.
Figure 16:
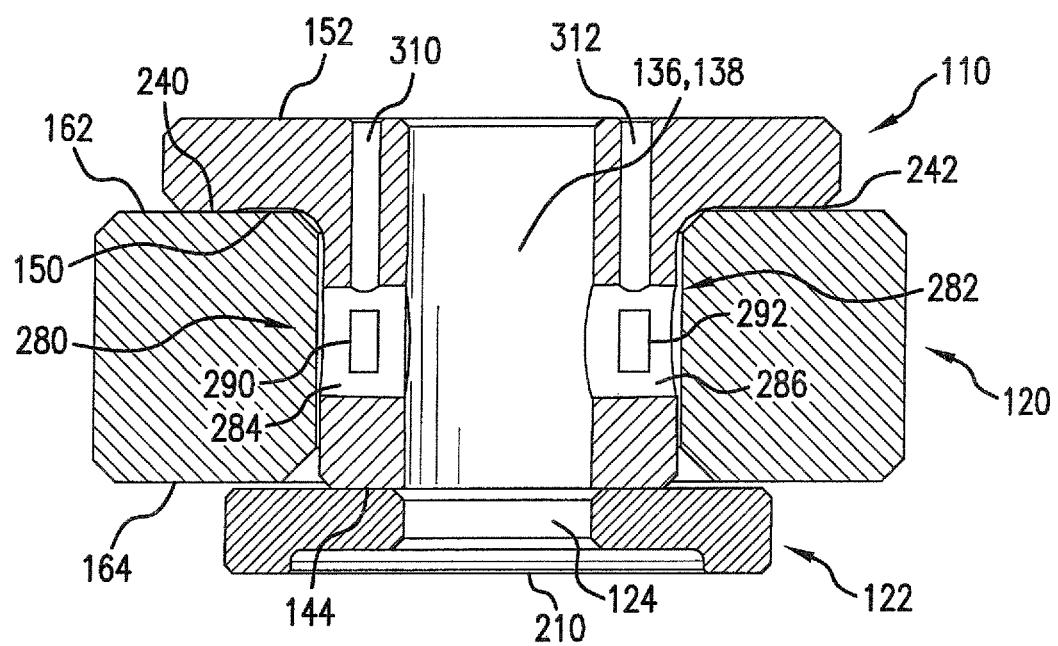
FIG. 16 is a sectional view taken along line 16-16 in FIG. 15.
Figure 17:
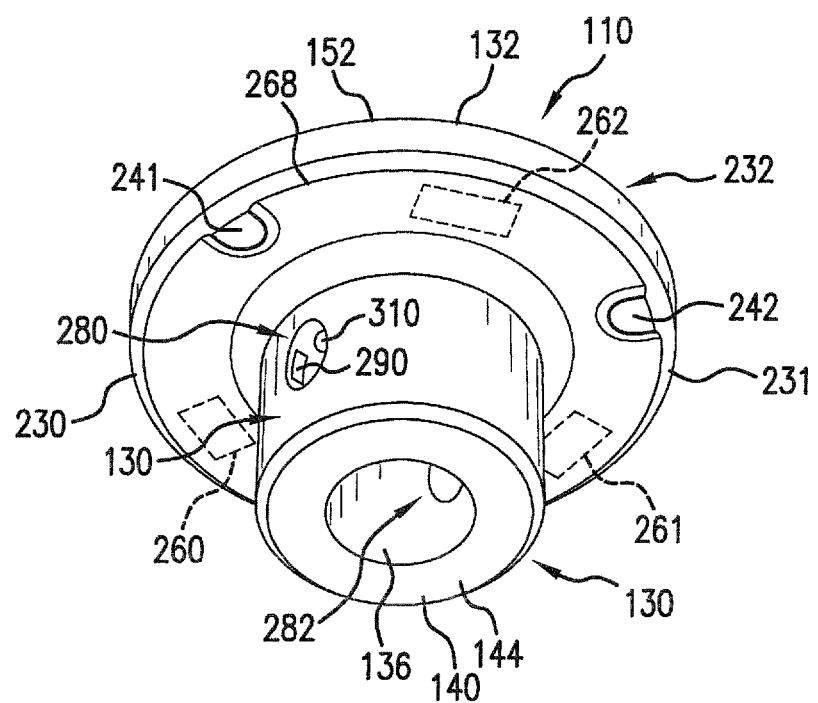
FIG. 17 is a bottom side perspective view of the strain collar shown in FIG. 15.
Figure 18:
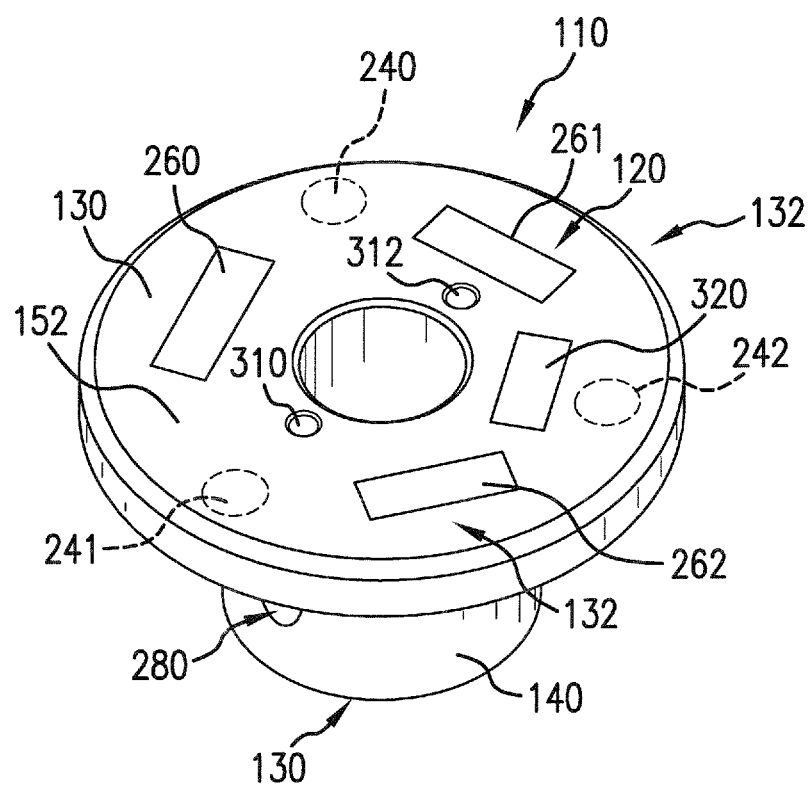
FIG. 18 is a top side perspective view of the strain collar shown in FIG. 17.

Referring now to the drawings wherein the showings are for the purpose of illustrating preferred and alternative embodiments of the invention only and not for the purpose of limiting same, FIGS. 1-5 show an example center-pull hoist ring or hoist device 10 for connection to a load member 12 shown in FIG. 2. The description below relating to hoist device 10 is only intended to provide general background for an example center-pull hoist ring that the invention of this application can be used in connection with wherein this description is not to be used to limit the invention of this application. The background of this application includes yet other rings that can be used with the invention of this application. Further, other figures of this application show another example center-pull hoist ring that can utilize the invention of this application.

The member 12 has a threaded bore 14 and an upper generally flat surface 16 for illustrative purposes. A hoist device supporting stud 20 includes an upper cylindrical head 22 with a cylindrical body portion 24 below head 22 and terminating in a lower threaded shank 26. The diameters of the head, cylindrical body portion and threaded shank are progressively decreased as illustrated in FIG. 2. Stud 20 is the load bearing member which must absorb both shear and tension in operation of hoist device 10. The stud is illustrated with a top surface 30 having a lower bearing surface 32 which is torqued against surface 16 when stud 20 is in its load supporting position. The undersurface of head 22 defines a downwardly facing load supporting shoulder 34 which is an annular shoulder or surface below the cylindrical surface 36 of head 22. Stud 20 is illustrated as having a recessed portion 38 between shank 26 and body portion 24 so that the threads can be properly machined into shank 26. A similar recess 39 divides head 22 from body portion 24.

To provide the swivel mechanism, a cylindrical base portion 40 is rotatably mounted on stud 20 after the stud has been passed through a central passage 42 of member 40. This central passage includes an upper recess 44 for capturing head 22 and has an upper shoulder 46 engaging shoulder 34 of head 22. This engagement is the force transmitting structure so that as member 40 is pulled upwardly shoulder 46 engages lower shoulder 34 of head 22 so the stud provides the lifting force for member 12. The base member also includes a plurality of counter sink bolt holes 50 for bolts 52. In the illustrated hoist ring, fixed bolts are employed; however, as shown in other configurations of the ring, two or four bolts could be employed for assembling the hoist device 10.

A continuous hoist ring 60 having an upper bight portion 62 and a straight cylindrical connecting portion 64 is provided by an appropriate process. In one version of the disclosed ring, hoist ring 60 is a continuous forged steel component. It could be a cast iron component or it could be formed into an appropriate shape from a single piece of steel and welded together. In accordance with the shown hoist ring, the ring can be a continuous ring.

In accordance with other aspects of the center-pull hoist ring, a cylindrical port member 70 matching generally the shape of base member 40 is provided with a slot 72 for capturing cylindrical portion 64 of ring 60 between base member and support member 70. A plurality of threaded bores 74 co-act with bolt holes 50 to allow bolts 52 to clamp the cylindrical body portions of members 40, 70 together in a manner which captures hoist ring 60 between the two members. These members rotate in unison about stud 20 while hoist ring 60 can pivot through approximately 180°.

Hoist device 10 has the advantages of the continuous ring type hoisting device as well as the swiveling action heretofore obtainable only in a clevis type of hoist device. The center-pull hoist ring does not clamp a bushing between stud 20 and surface 16. Of course, such a bushing could be employed in some arrangement which would still obtain the advantages.

In practice, a socket is provided in the top 30 of head 22 for the purpose of using an Allen wrench for assembling stud 20 into threaded bore 14 on load member 12.

In accordance with other aspects of the shown center-pull hoist ring, the socket can be replaced by the diametrically extending passage shown as a bore 80 through head 22. To assemble stud 20 into bore 14, bolts 52 assemble members 40, 70 for capturing stud 20 in recess 44 and cylindrical connecting portion 64 in slot 72.

The center-pull hoist ring as illustrated includes an arrangement for pivoting ring 60 as well as swiveling ring 60 by the swiveling action of the members 40, 70 after they have captured the stud and the connecting portion 64 of lifting ring 60.

While applicant has gone into particular detail to describe and define a particular style of center-pull hoist ring, this has been done only to provide background on the general characteristics of center-pull hoist rings and is not intended to limit the invention to this particular hoist ring. In this respect, the invention of this application that will be discussed more below is configured to work in connection with a wide range of hoist rings, in particular, a wide range of center-pull hoist rings wherein the description above and the corresponding figures, are intended to be illustrative and not limiting. Yet further, the invention of this application can be configured to work with a wide range of existing hoist rings without requiring significant design changes to the general structure of hoist ring and one of which will be discussed more below.

With reference to FIGS. 6-20, shown preferred sets of embodiments of the invention of this application. While other embodiments shown in the provisional applications are not shown in this application, they are contemplated wherein applicant reserves the right to pursue one or more of these alternative embodiments in a separate application wherein this specification is intended to streamline prosecution, but not limit the invention.

In greater detail, shown in these figures is a representative center-pull hoist ring 100 that includes certain embodiments of the invention of this application. In these embodiments, ring 100 includes one or more strain sensor or gauges to detect loads; some of which independently of others. In this respect, ring 100 includes a strain collar 110 configured to detect loads applied to the hoist ring. These loads include, but are not limited to, tightening loads to ensure that the hoist ring bolt is properly tightened to the load with a desired bolt holding force or load, applied loads to warn if the applied load is too great, shock loads to warn if the ring has been subjected to a large shock load, bail angle or load angle to make sure the load angle is not outside a predetermined range, and/or other loads.

Ring 100 includes a hoist ring body 120, strain collar 110, and a base washer 122 with a washer opening 124. Ring 100 can further include an electronics cap 126 that can cover the electronics that will be discussed in greater detail below. In addition, cap 126 can include one or more display functions, including any of the display functions discussed below, that can alert the user of the loads being applied to the ring. Cap 126 can substantially cover an exposed portion of strain collar 110 as is shown, but this is not required. Ring 100 further includes a bail or U-bar 128. However, while one particular type of U-bar is shown in the drawings, any ring like structure known in the art could be utilized with the invention of this application wherein the term U-bar 128 is intended to be broadly interpreted to include all ring or hook like structures use for hoisting devices. The components discussed that relate to commonly used ring components will not be disclosed in detail in the interest of brevity. U-bar can be joined to ring body by any method known in the art including, but not limited to, U-bar pins 127 and held in place by locking pins 129.

Strain collar 110 includes a stem portion 130 and a flange portion 132 that will be discussed in greater detail below. While not required, flange portion can be an upper portion in reference to a typical load being positioned below ring 100. For this application, and with reference to the orientation of the drawings, the flange and other components of ring 100 are described as upper and lower in reference to the drawings. But, the invention is not to be limited in view of this description. Stem portion 130 has an outer stem surface 134 and in one embodiment this outer surface is cylindrical. Stem portion further includes an inner bolt opening 136 defined by an inner stem surface 138. Inner stem surface 138 also can be cylindrical. These inner and outer stem surfaces define a stem wall 140 that extends about a stem axis 142 and which has a thickness. Stem portion 130 and stem wall 140 have a bottom extent 144 and an opposite top extent 145. Bottom extent 144 is opposite of flange portion 132 and faces washer 122. Bottom extent engages washer 122 when ring 100 is tightened onto the object to be lifted. Flange portion 132 generally extends from top extent 145.

Flange 132 includes a lower flange surface 150 and an upper flange surface 152. It is preferred that strain collar 110 includes a radius 154 between lower flange surface 150 and outer stem surface 134. In a preferred set of embodiments, radius 154 is between 0.050 inches and 0.200 inches wherein preferably radius 154 is between about 0.070 and 0.110 inches. This radius can be used to help control stresses and/or the deflection from the pads. Washer 122 has a top washer surface 156 and a bottom washer surface 158. Bottom extent 144 engages top washer surface 156.

Ring body 120 includes a ring body opening 160 that extends from a body top extent 162 to a body bottom extent 164 and is sized to fit over outer surface 134 of stem 130. As a result, body 120 extends about stem surface 134 and is between lower flange surface 150 of flange portion 132 and top washer surface 156 of base washer 122. Stem 130 has a stem length 170 that allows body 120 to rotate about a ring axis 172 even when the ring is tightly connected to an associated object (not shown). This length also directs bolt tightening forces of the device to the stem, which will be discussed more below. In one set of embodiments, ring axis 172 is coaxial with stem axis 142. Again, while it is preferred that flange portion 132 is an upper flange portion (wherein upper and lower in this application merely refers to the position in the drawings), strain collar 110 of this application could be inverted without detracting from the invention of this application and flange portion 132 could be a lower flange portion.

Ring 100 further includes a bolt 190 that is configured to secure the ring to the associated object to be lifted (not shown). Bolt 190 can be any fastening device that is used in the art. The bolt shown includes a bolt head 192 and a threaded shaft 194 wherein bolt head 192 can include a tool receiving feature 196. Bolt 190 can further include a snap ring groove 200 that can work in connection with a snap ring 202 to secure the bolt and ring 100 in an assembled condition while allowing relative rotation. According to another set of embodiments, fastener 202 could be a Tinnerman one-way self locking nut and/or grooveless retainer ring. These devices can be utilized to eliminate snap ring groove 200. Washer 122 can further include a snap ring recess 210 extending into bottom washer surface 158 that allows the snap ring to be counter sunk and positioned away from the applied loads.

Bolt 190 is configured such that threaded shaft 194 extends through both inner bolt opening 136 and washer opening 124, but it is spaced from body 120 to allow relative rotation of the body 120 and bail or U-bar 128.

With special reference to FIGS. 14, 17 and 18-20, the ring shown in these embodiments measures loads by way of measuring strain in different locations within strain collar 110. In this respect, strain collar 110 includes one or more deformation zones configured to create controlled elastic deformation that can be measured to determine different applied loads. In the embodiment shown, ring 100 has a first deformation zone 220 in flange portion 132 and a second deformation zone 222 in stem portion 130. These zones can work independently and/or in combination to calculate applied loads on ring 100. Further, each of these deformation zones can include one or more planned deformation areas, which will be discussed more below. As can be appreciated, multiple planned deformation areas can be used to improve accuracy by comparing and/or averaging measured values, but also can be used to vector a direction of applied loads.

With reference to first deformation zone 220, flange portion 132 can be divided into multiple deformation areas. As is shown in this example, there can be three deformation areas 230-232. However, while three deformation areas are shown, the invention could have more or less deformation areas without detracting from the invention. Furthermore, while three areas are shown since three is considered a minimum number for vectoring; the invention of this application can have more or less areas and/or zones depending on the desired load to be monitored, the accuracy needed for vectoring, averaging needs and/or costs.

Deformation areas 230-232 are controlled elastic deformation areas that are produced by three deformation pads 240-242 on lower flange surface 150 of flange portion 132. As can be appreciated, if there are a different number of deformation areas, there could be a different number of deformation pads wherein this description is to be considered an example only. In greater detail, bolt head 192 (or a washer below head 192), engages upper flange surface 152 in zone 236 and deformation pads 240-242 engage body top extent 162 of body 120 when there is an applied load on ring 100. Thus, this applied load is directed directly into flange portion 132 at three designated points and these are all known points. In that pads 240-242 are radially spaced from zone 236, elastic deformation is caused in deformation areas 230-232 and flange portion 132 further includes three flange strain gauges 260-262 that are configured to measure the elastic deformation in areas 230-232. Flange strain gauges 260-262 can be located on upper flange surface 152, but this is not required. Further, in one set of embodiments, lower flange surface 150 includes a circumferential edge 268 and pads 240-242 are circumferentially spaced about axis 172 at or near edge 268. It is preferred that pads 240-242 are equally spaced about axis 172 at or near edge 268. As can be appreciated, the strain gauges measure the deformation of areas 230-232 and this data can be used to determine the load that is applied to ring 100. Further, by having multiple strain gauges, the direction of the load can be determined. This information can be used to determine if the ring is within its designed limits by different measured loads from each gauge. As will be discussed more below, the number of strain gauges per deformation area can also be increased and the location of these gauges can be altered without detracting from the invention of this application.

According to yet another set of embodiments, stem portion 130 can include an outer stem surface 134 that is formed at a stem angle 270 relative to axis 142 wherein outer stem surface 134 can include a conical surface portion. While preferably, all, or substantially all, of outer stem surface 134 is formed at the stem angle, this is not required. A conical surface configuration can work to enhance the action of deformation of areas 230-232 by allowing a limited amount of tilt or rock in the stem to help determine the bail angle of the U-bolt. Stem angle 270 is configured such that stem surface 134 extends upwardly and inwardly wherein bottom extent 144 has a larger diameter or size than top extent 145. Stem angle 270 can be between 0 degrees and 10 degrees. In a preferred embodiment, stem angle is between 0 degrees and 5 degrees. More preferably, stem angle 270 is between 1 degree and 3 degrees.

Second deformation zone 222 is located in stem portion 130 wherein stem portion 130 includes load sensor arrangements 280 and 282. Load sensor arrangements include strain openings 284 and 286 that will deform when a load is applied. In the embodiment shown, second zone includes two oval or elliptical holes or strain openings 284 and 286 producing two load sensor arrangements; however, more than two load sensor arrangements could be used. In one set of preferred embodiments, a single load sensor arrangement 280 is utilized. Again, these openings are designed for controlled elastic deformation and include stem strain gauges 290 and 292, respectively, positioned therein to measure the amount of deformation. While this zone is shown with only a single strain gauge per opening, each opening could include multiple strain gauges without detracting from the invention of this application. In one set of embodiments (not shown), each opening includes two strain gauges. Second deformation zone 222, is configured to determine the tightening load of the ring and not the applied load on ring 100 or the load angle of the applied load. This is the reason for less than three strain openings since tightening load magnitude is only needed. Having two load sensor arrangements both increases accuracy of the measurement and generally balances the load structure in the stem. In greater detail, the second zone is configured to calculate the tightening force that is applied to bolt 190 as it is threaded onto the object to be lifted. In that body 120 has a height or thickness 296 that is less than the stem length 170, stem 130 engages washer 122 when the bolt is tightened and the tightening load passes through stem 130. As a result, body 120 is generally isolated from the tightening load. This also allows body 120 to freely rotate about axis 172 even when ring 100 is fully tightened onto the load to be supported. Continued tightening of bolt 190 deforms strain openings 284 and 286 that include strain gauges 290 and 292. The amount of deformation of openings 284 and 286 can then be used to calculate the tightening load applied to bolt 190. This data can be used to alert an end user that bolt 190 is properly tightened onto the object to be lifted. In addition, since body height 296 is less than the stem length 170, tightening bolt 190 does not significantly affect first deformation zone 220 since pads 240-242 are maintained in a generally spaced relationship with body 120 during bolt tightening. However, it has been found that preferably openings (284 and/or 286) are in alignment with one of the three deformation pads to balance forces on the ring.

In order to electrically connect the electronics of ring 100, strain collar 110 can include wire openings or holes 310 and 312 that extend from upper flange surface 152 to strain openings 284 and 286, respectively. Openings 310 and 312 can allow strain gauges 290 and 292 to be in direct-electronic communication with electronics 320 positioned on upper flange surface 152. Electronics 320 can be any electronics discussed in this application including, but not limited to, those needed to operate the strain gauges, store data from the strain gauges, communicate data and provide a power supply. Electronics cap 126 can cover electronics 320 to create a sealed electronics cavity 322. Cover or cap 126 can include visual features to alert the user of the rings of this application of proper and/or improper uses of the hoist ring, which is discussed more below. Further, cover 126 can include connection port(s) to transfer data and charging ports to charge internal batteries.

According to yet another set of embodiments, ring 100 can include one or more accelerometers 324 that can be utilized for multiple functions. More particularly, accelerometer 324 can be utilized to measure shock loads. This measurement can be done independently of other sensors in ring 100 and/or in combination with other sensors. Accelerometer can also be utilized to help determine the positioning of ring 100 by detecting the movement of the ring and can be utilized to help determine the orientation of the ring. These functions can help with the determination of bail angle and also the overall lifting angle when compared with the bail angle data. Yet further, accelerometer 324 can be utilized as a back up to help in the determination of the bail angle. As can be appreciated, the overall sensor reading can therefore be utilized to calculate and/or determine many lifting parameter associated with the use of the ring and these can be utilized to determine the condition of the ring for future lifts and/or service intervals.

Figure 20:
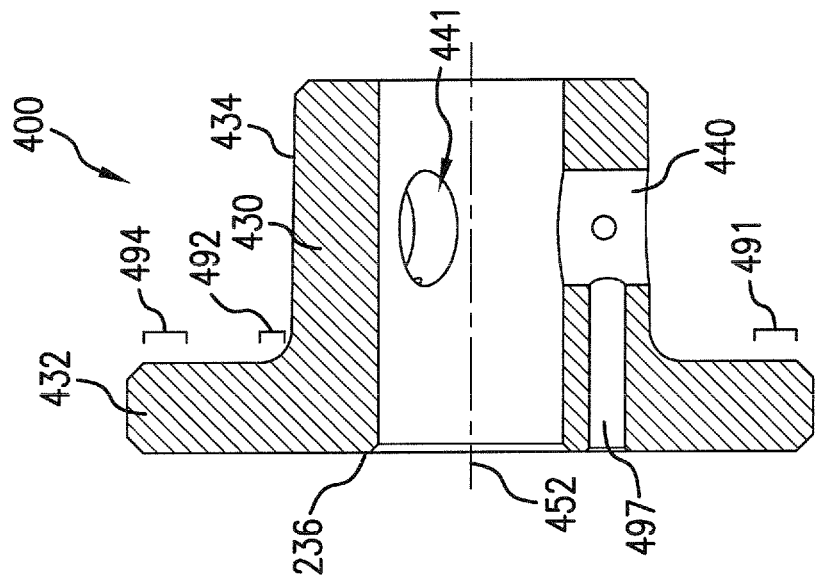
FIG. 20 is a sectional view taken along line 20-20 in FIG. 19.
Figure 19:
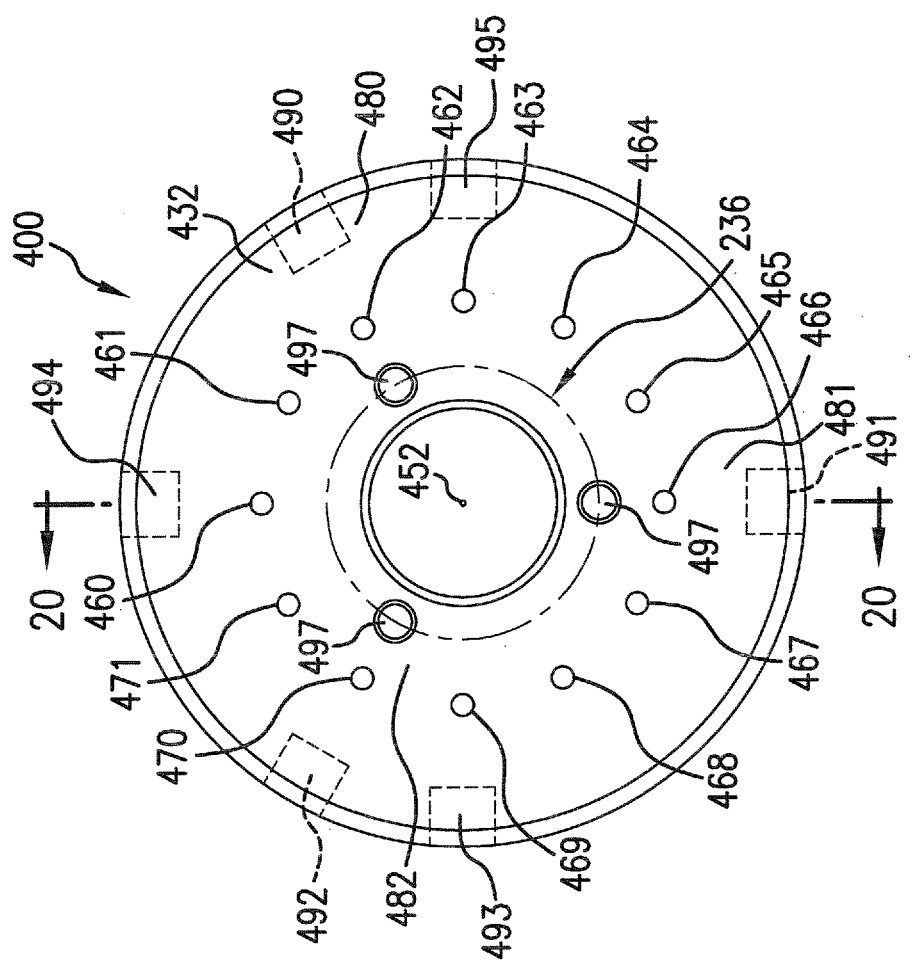
FIG. 19 is a top view of the strain collar shown in FIG. 17 showing alternative embodiments.
Figure 21:
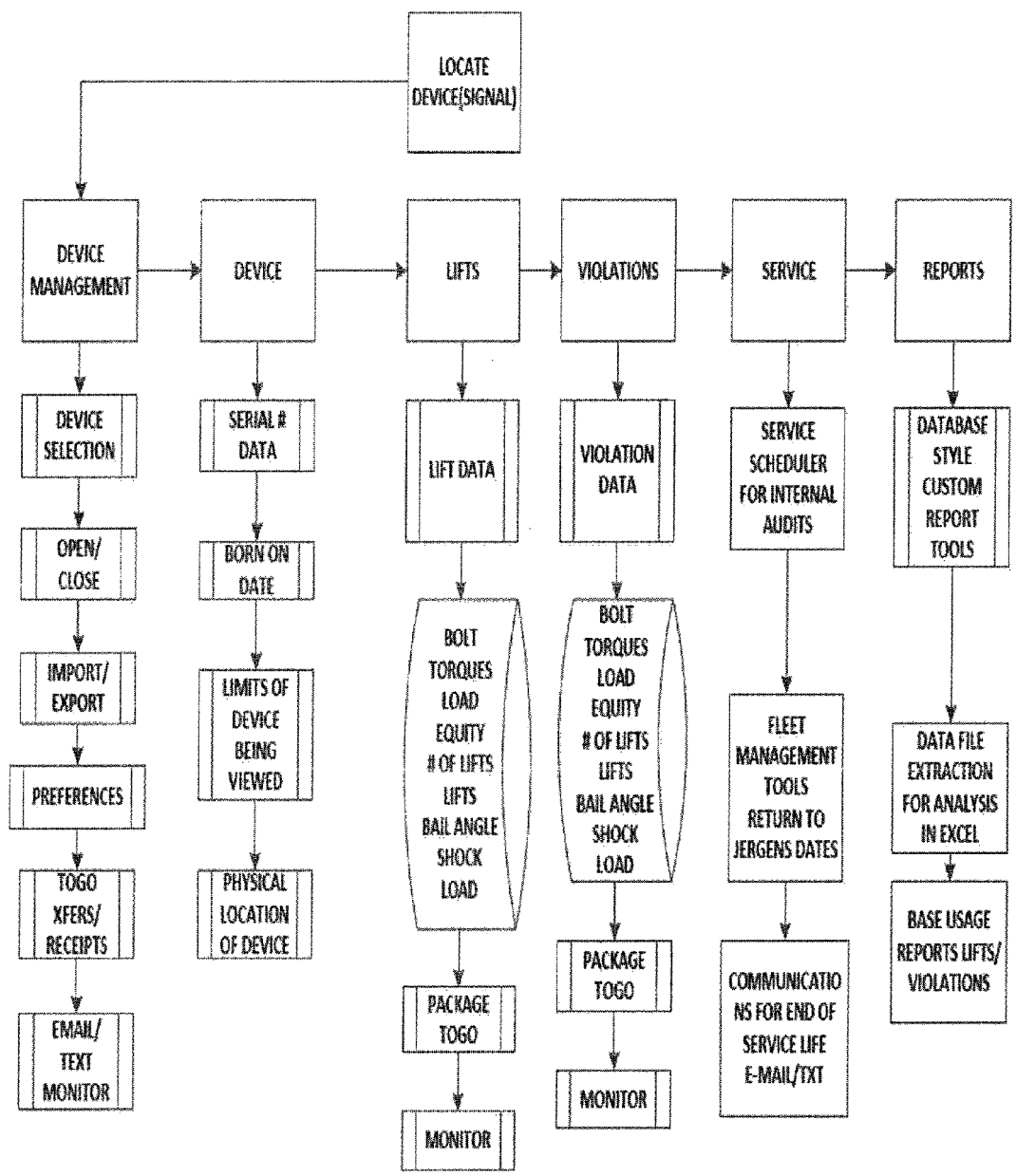
FIG. 21 is a flow diagram and flow chart for a central monitoring arrangement.
Figure 22:
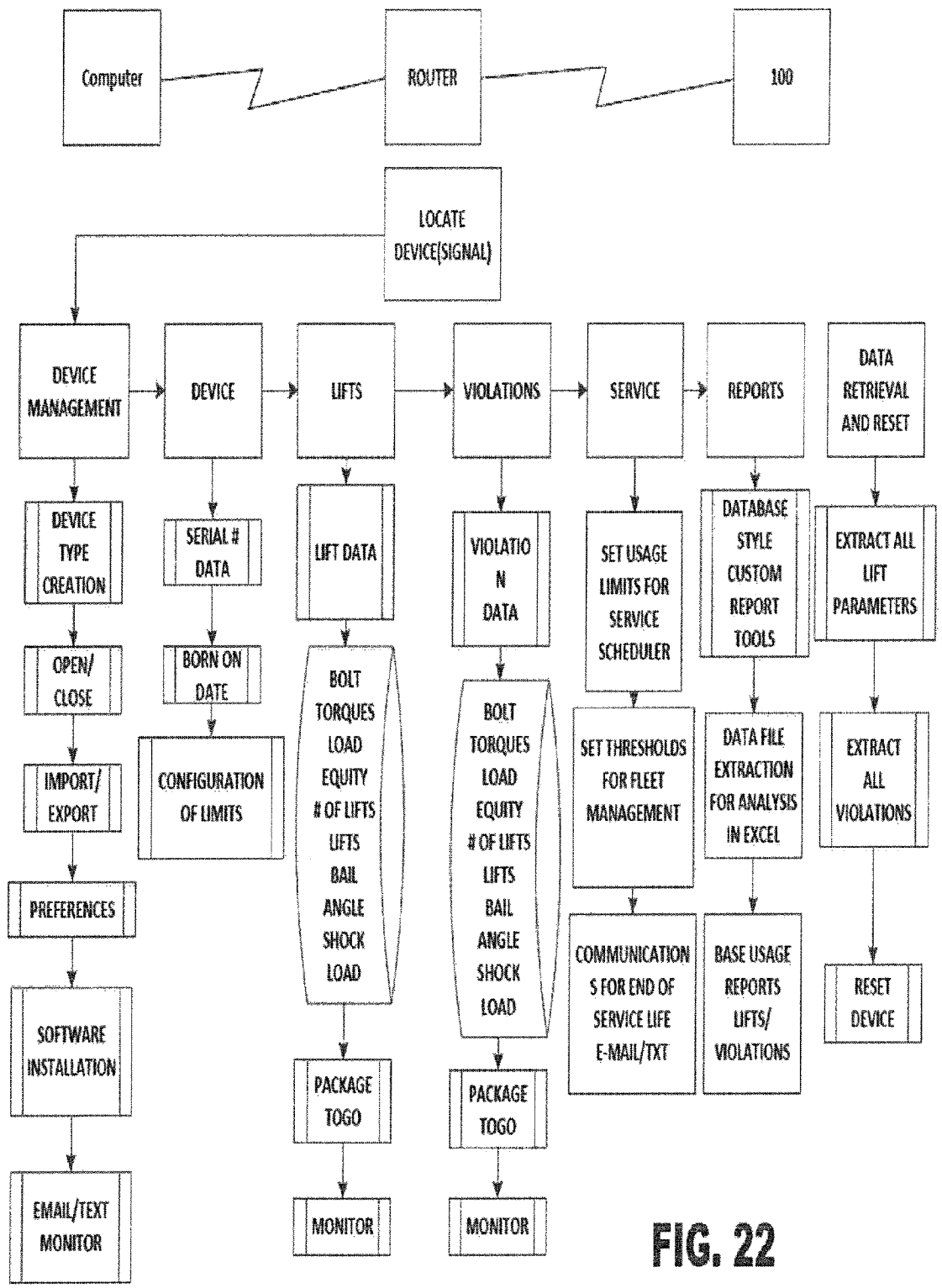
FIG. 22 is a flow diagram and flow chart for a configuration and service station.
Figure 23:
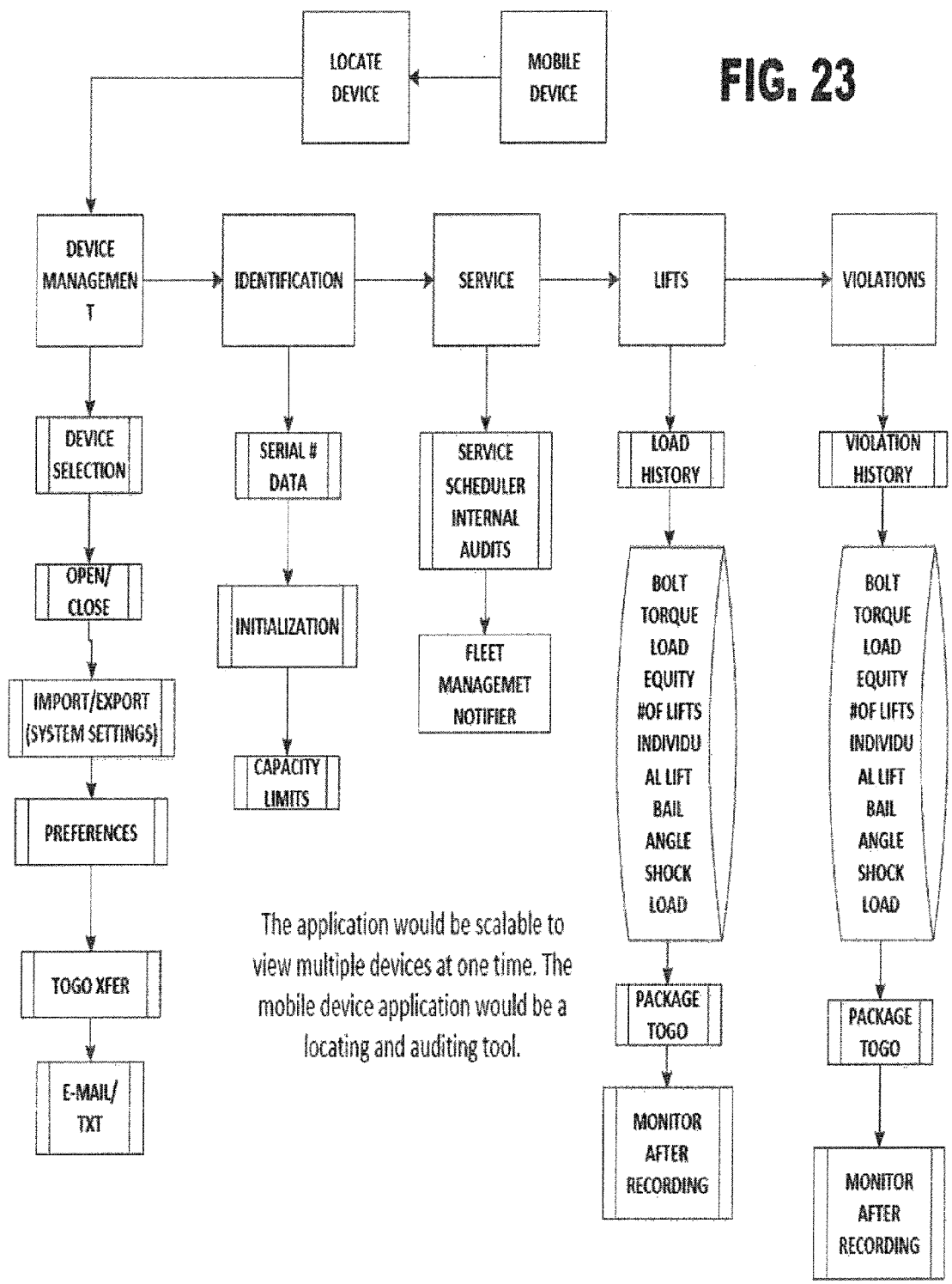
FIG. 23 is a flow diagram and flow chart for a mobile device application.
Figure 24:
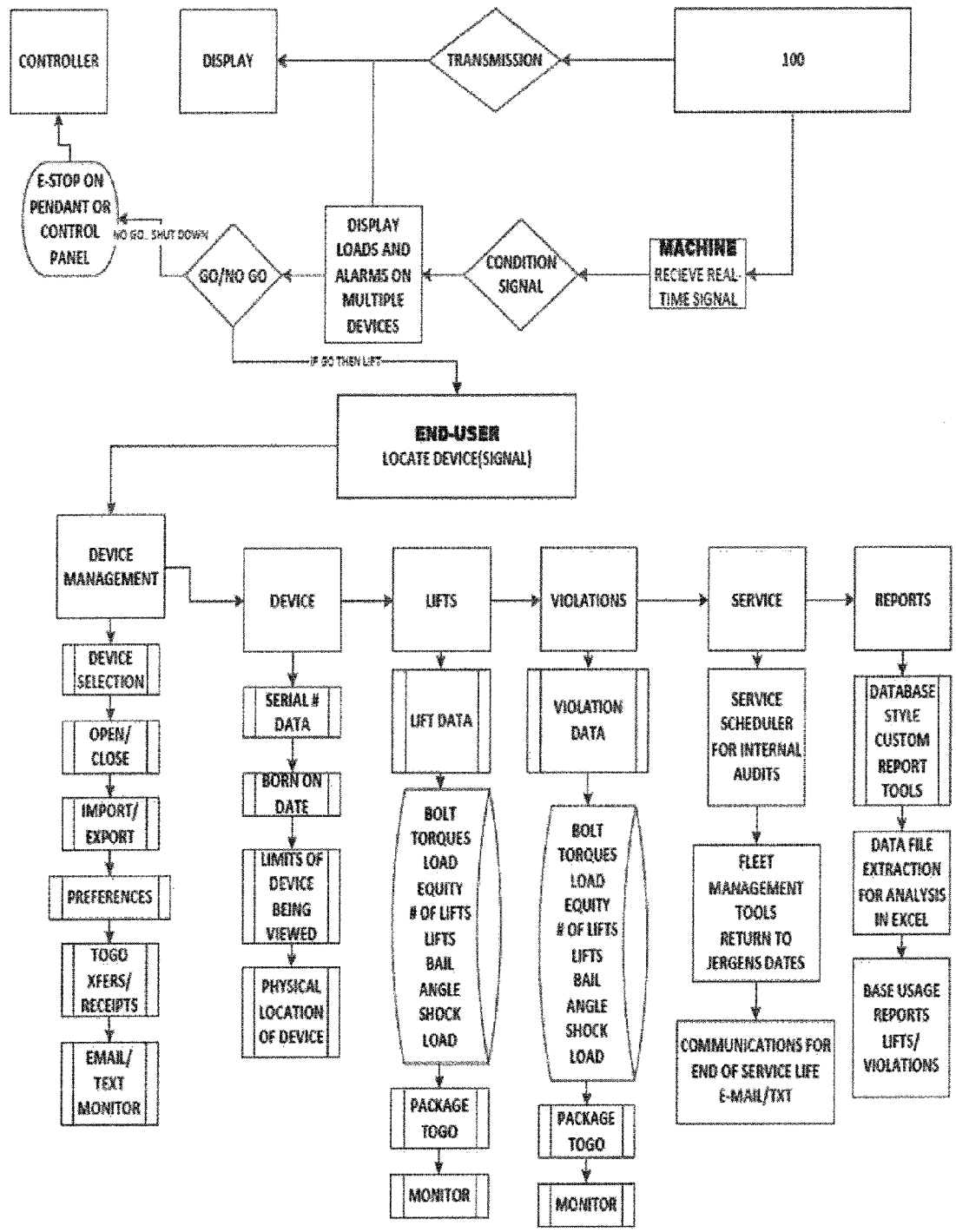
FIG. 24 is a flow diagram and flow chart for a real-time monitoring system.

With reference to FIGS. 19&20, shown is a strain collar 400 showing that multiple strain gauges could be used in each of the deformation zones. Further, strain gauges could be unidirectional gauges having a specific orientation. In these two figures, the gauges shown for these sets of embodiments include arrows to show the direction or orientation of the unidirectional strain gauges. In greater detail, collar 400 can be similar to any of the embodiments described above wherein this discussion will be limited to strain gauge placement and orientation in the interest of brevity. As with the collars described above, strain collar 400 includes a stem portion 430 and a flange portion 432. Stem portion 430 has an outer stem surface 434 that can be cylindrical or conical as is discussed above in greater detail. Further, in this embodiment stem portion 430 includes three strain openings (440 & 441 are shown) that operate as described above. As is discussed above in greater detail, one or more strain opening could be used without detracting from the invention of this application. Yet even further, if tightening forces are not to be calculated, collar 400 could even have no stem strain openings. As is best shown in FIG. 20, and with reference to strain opening 440, strain collar 400 can include one or more stem strain gauges that are unidirectional and oriented parallel to a stem axis 452.

Turning to flange 432, and FIG. 19, strain collar 400 can utilize one or more strain gauges per deformation zone. In this set of embodiments, shown are twelve strain gauges that are positioned about axis 452. In greater detail, strain gauges 460-471 are shown wherein there are multiple strain gauges for each zone 480-482. Collar 400 shows both a three deformation system wherein collar 400 has pads 490-492 on the lower flange surface as is described above and a four pad system, which will be described below. Further, collar 400 includes multiple sensors for each zone. While a three pad system is shown, the system could utilize a wide range of pads including, but not limited to, three, six, nine or more sensors without detracting from the invention of this application. With respect to a four pad system, collar 400, or other collars of this application, could utilize four pads, such as pads 491, 493-495 thereby creating a four zone system. Again, one or more strain gauges could be utilized per zone in the four pad system wherein these figures are examples only for multiple gauges per zone. Further, more or less zones could be used to both determine applied loads and to determine the bail or lifting angle of the ring without detracting from the invention of this application. As is also shown in these figures, the location and/or orientation of the strain gauges could be modified to adjust the results of the device. In a preferred set of embodiments, one or all of strain gauges 460-471 are oriented as is shown with respect to gauge 462 wherein the unidirectional strain gauge is oriented radially outwardly from axis 452. However, as is shown with respect to gauges 460, 461 and 471, different orientations could be utilized without detracting from the invention of this application. Yet further, in this set of embodiments, if three pads are used and three gauges are used, gauges 462, 466 and 471 could be utilized in the orientation shown for gauge 462 wherein this set of embodiments includes gauges positioned over the pads. As can be appreciated, the number of strain openings and corresponding stem strain gauges can influence the number and location of the one or more wire openings 497. As is discussed more above, these wire openings can be used to allow wired communication between the stem strain gauges and the electronics that are above the strain collar.

While not shown, other embodiment could include one or more load disk (not shown) that could be configured to work in combination with the hoist ring. As with other aspects of the invention, the load disk could be utilized with other electronics, software and hardware, to monitor applied loads. These electronics can further include a range of components to perform a wide range of tasks as needed to monitor the use of the hoist ring, store the data acquired, analyze the data and/or report the data. The disk and/or system can utilize a wide range of other electronics to create the data used for the review and analysis of the service of the hoist ring. Again, the load disk, or other embodiments of this application, could be configured to house all electronics of the device including, but not limited to the sensors, the data store, the CPU, the output/input electronics and/or other electronic and sensing devices. Further, the load disk, or other systems of this application, could include a power supply to run them, output/input data transfer devices to communicate and/or store the data generated by the sensor(s) in the system.

Since the load data can include separate measurements of the hold down load or force of the hoist ring bolt and the lifting load of the load being lifted, the system can dynamically measure a wide range of elements relating to the lift and the hoist ring.

The ring can include one or more warning lights that can come in many forms. Further, cap or cover 126 can include a large dome shaped disk portion that can house light sources, such as LED lights, that light all or part of the dome portion of the disk in response to an event. For example, a green light(s)

can be used to communicate a "Go" condition, yellow light(s) can communicate that a predetermined level is being approached and red light(s) can communicate a "Stop" condition wherein a predetermine measurement or load has been met or surpassed or not yet met.

More particularly, the first and second zone sensors can be utilized to provide one or more visual or audible indicators concerning the torque of applied to the bolt, the lift in range, the equality of the load, shock loading, bail angle (applied load effect), report service needed and/or generate or report other data. This can be accomplished by using data from a desired selection of the sensors based on predetermined conditions and communicating the data to lights located in/on the disk and/or located in the remaining structural components of the hoist ring, or even in remote systems. Yet further, this date could also be communicated to systems external to the ring to alert personnel away from the actual lift itself, such as supervisors, ring manufacturer and/or maintenance workers. For example, ring 100 can be in communication with a portable device, such as an arm band, that includes the same lighting features as the ring and other features. Yet further, the external systems can provide details, beyond warning lights, such as actual lifting loads and bail angles figures. This kind of communication can include any technology known in the art, or known in the future, including, but not limited to Near Field, hard wired cable systems, RF, GPS, WI-FI, Bluetooth, local area networks, the internet, cellular technology and/or satellite technology.

The light feature can be a lighted dome that can be utilized for multiple types of event indicators. Ring 100 can include separate light indicators such as a first set of lights 340 for bolt torque or holding force and a second set of lights 342 for lifting loads. Each set can include multiple lights based on a wide range of parameters. For example, light set 340 can inform the end user when the bolt of the hoist ring is properly tightened based on pre-determined parameters. As can be appreciated, these parameters can be different for different size rings and/or different style rings. More particularly, light set 340 can include a red light 350, a green light 352 and a yellow light 354. For example, yellow light 354 could provide a visual confirmation that a tightening load has been detected, but that optimal torque or holding load has not been achieved. As bolt is tightened, yellow light 354 would remain illuminated until a desired bolt torque range is achieved wherein yellow light 354 would be turned off and green light 352 would be illuminated. Then, if tightening is continued, red light 350 would be illuminated if the desired torque range is exceeded. Other combinations of lights are also contemplated without detracting from the invention of this application that includes less than three lights. For example, green light 352 could be illuminated to provide a visual confirmation that the load has been detected, but that optimal torque or holding load has not been achieved. Then, red light 350 could be illuminated until the desired range is achieved. Then, when the desired range is achieved, red light 350 would go out and green light 352 would be illuminated. If the bolt is over tightened, red light 350 could be illuminated again. Or, in another possible alternative, green light 352 could flash when the initial load is detected and then stay on when the desired load is reached. As can be appreciated, any combination of lighting could be utilized to correspond with an event and/or load without detracting from the invention of this application. Even gauges could be utilized. Below are some additional examples of lighting sequences.

Light set 342 can be utilized to provide visual confirmation relating to the lifting load. Again, while a three light system is shown, three lights are not required. In this respect, light set 342 could include a red light 360, a green light 362 and a yellow light 364. Green light 362 could be illuminated, for example, when a lifting load is detected. Or, when a tightening load is detected when bolt 190 is tightened onto the object to be lifted and/or secured. Then, green light 362 would remain illuminated if the load is maintained below predetermined limits. Then, if any load, bail angle and/or load/bail angle combination exceeds the predetermined limits; red light 360 would be illuminated. In addition, yellow light 364 could signal that the load limit is approaching. Further, if any event is encountered that would require the ring to be serviced; one or more lights could remain illuminated or flash after the load is removed. This occurrence also could be recorded in the data store for future reference.

According to one set of embodiments, the disk and system includes the following capabilities:
Evaluation for bolt tension or holding force
Evaluate for equality of load
Evaluate actual lift against known
Detection of Shocking
Detection of Bail Position or angle
  Based on the evaluation of loads against known criteria a series of lights will be illuminated, as a visual queue to the end-user.
  Bolt torqued properly . . . Red=Stop, Green=Yes
  Equality of load . . . Red=Stop, Green=Go
  Shock load . . . Red=Stop, Green=Go
  Value of load . . . Red=Stop, Green=Yes
  Applied load . . . Red=Stop, Green=Yes
  Value, shock and applied will be tied together into one set of lights.
The device can also include memory capability and/or communication capability to store data, such as the number of lifts and the parameters of each lift and then communicate them to one or more service modules. Further, the memory can be configured so that it is only accessible by authorized personnel.
If a red or warning light is activated while in service, the end-user is required to remove the device from service and send to the hoist ring for service/evaluation. If the ring is not sent for service/evaluation, this data can be stored too.

The hoist ring device can further include an on board custom developed device hardware that can interact with a communication and calibration software package.
  The communication and calibration software package can allow a new hoist ring to be initialized and/or communicate with an existing hoist ring device to obtain the information, such as the following stored information.
Serial Number
Date Purchased
"Born On"
Owner
Time and Date stamps
# of Lifts
Individual load snap shot
Load value of each lift
Shock value associated with a lift
Applied loads
Bolt Torques
This kind of data is valuable for determining service life and service intervals, failure analysis, and even future product improvements.

In yet other embodiments of the invention of this application, the system can include software and/or software applications for computing and/or mobile computing devices to allow an end-user in a desired proximity of the lifting device and/or system to query specific data relative to the following:
- Time and Date Stamp
- Bolt torque
- Individual load snap shot
- Equality of lift average
- # of lifts
- Value of load on each lift
- Applied loads
- Shock loads and values
- Serialization information
  - Date built
  - Date purchased
  - Serial number
  - Lot #
  - Life cycle value A warning light will notify the end user and/or authorized personnel that the device is required to be removed from service and sent to an authorized service provided for service and/or evaluation.

In yet further embodiments of the invention of this application, the system can include software and/or software applications to allow multiple hoist rings to communicate with a single computing and/or mobile computing devices to allow an end-user in a desired proximity of the lifting device and/or system to query specific data as noted in this application. For all applications and embodiments, these computer devices can be linked to one or more hoist rings by any communication medium currently known or known in the future including, but not limited systems utilizing RF, GPS, WI-FI, Bluetooth, local area networks, the internet, cellular technology and/or satellite technology. Yet further, the multiple hoist rings could communicate with multiple computing systems.

In another set of embodiments, the hoist ring and system can work with specialized hardware. In this respect, a hoist ring according to one or more embodiments and/or aspects of the invention of this application can work with additional hardware and software combinations that can monitor in real time the load being applied from multiple lifting devices on one load. The dynamic measurements could be evaluated by the on-board CPU, a remote CPU. Yet further, the data could be aggregated and evaluated by a computing device CPU and can be tied to other devices such as a crane E-Stop Switch. Therefore, if any over load conditions are detected, the crane could be automatically stopped. As can be appreciated, while a crane is a good example, it is not the only example of the uses of the invention of this application and/or the incorporation of the invention of this application into other equipment and systems.

Yet further, the systems of this application is not limited to lifting wherein the systems could be utilized for other applications including, but not limited to, custom lifting systems, work holding devices, machine tool adaptive control technologies, and critical fasteners.

With reference to FIGS. 19-22, shown are several methods of using the inventions of this application.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation. Further, while the invention is shown and describe as more of a center-style device, it could also be used as a side-pull device and can be used in other center and/or side pull device.

It is claimed:

1. An intelligent hoist ring configured to monitor and/or detect an applied load, the hoist ring comprising: a ring body including a U-bar, the U-bar being configured to receive an associated applied load and direct the associated applied load to an associated object, the ring body extending between a first body extent and a second body extent and having a central body opening extending between the first and second body extents, the first and second body extents defining a body thickness; a strain collar having a stem portion and a flange portion, the stem portion extending from a first stem extent to a second stem extent, the stem portion extending along a stem axis and having a radially outwardly facing outer stem surface and a radially inwardly facing stem bolt opening defining a radially inwardly facing stem surface, the radially inwardly facing stem bolt opening and the radially outwardly facing stem surface defining a stem wall and the stem wall extending about a stem axis, the first and second stem extents defining a stem length, the strain collar having a flange portion extending radially outwardly from the first stem extent, the flange portion having a flange surface facing toward the second stem extent that is generally transvers to the stem axis, the flange surface having at least one deformation pad to produce a controlled elastic deformation of the flange in at least one flange deformation zone, the controlled elastic deformation being in response to the associated applied load on the U-bar, the strain collar having a flange strain gauge in the at least one flange deformation zone configured to detect the associated applied load; the hoist ring further including a base washer having a first washer surface and a second washer surface, the base washer further including a washer bolt opening extending between the first and second washer surfaces, the base washer being configured to engage the second stem extent; the hoist ring further including a hoist ring bolt configured to extend through the stem and washer bolt openings and threadingly engage the associated object; the central body opening being shaped to receive the stem portion of the strain collar, the base washer capturing the ring body between the first washer surface and the flange surface of the strain collar.

2. The intelligent hoist ring of claim 1 further a position sensor for determining the bail angle of the U-bar.

3. The intelligent hoist ring of claim 2 wherein the at least one deformation pad to produce the controlled elastic deformation of the flange in the flange deformation zone is at least three deformation pads, the at least one flange deformation zone being at least three deformation zones, the flange strain gauge being at least three flange strain gauges configured to detect the associated applied load and an angle of the applied load, the at least three at least three flange strain gauges forming at least part of the position sensor.

4. The intelligent hoist ring of claim 3 further including an accelerometer, the accelerometer forming at least part of the position sensor.

5. The intelligent hoist ring of claim 2 further including an accelerometer, the accelerometer forming at least part of the position sensor.

6. The intelligent hoist ring of claim 2 further including a bail angle sensor forming at least part of the position sensor.

7. The intelligent hoist ring of claim 2 wherein the bail angle sensor includes a rotary angle sensor.

8. The intelligent hoist ring of claim 2 further including a washer sensor to determine the position of the washer relative to the U-bar.

9. The intelligent hoist ring of claim 2, wherein the radially outwardly facing outer stem surface of the stem portion includes a conical surface portion, the conical surface portion extending inwardly toward the first stem extent, the conical surface portion extending inwardly at a stem angle and the stem angle being between 0 degrees and 5 degrees.

10. The intelligent hoist ring of claim 9, wherein the stem angle is between 1 degree and 3 degrees.

11. The intelligent hoist ring of claim 1 wherein the at least one deformation pad is a plurality of deformation pads equally spaced about the stem axis.

12. The intelligent hoist ring of claim 11 wherein the flange surface has an outer circumferential edge, that plurality of deformation pads being at least near the circumferential edge.

13. The intelligent hoist ring of claim 1 wherein the at least one deformation pad to produce the controlled elastic deformation of the flange in the flange deformation zone includes three deformation pads equally spaced about the stem axis, the at least one flange deformation zone including three deformation zones equally spaced about the stem axis and between the three deformation pads, the flange strain gauge including three flange strain gauges in the three deformation zones.

14. The intelligent hoist ring of claim 1 wherein the stem portion includes a load sensor arrangement having a strain opening and a stem strain gauge secured relative to the strain opening.

* * * * *